(12) United States Patent
Hausdorff et al.

(10) Patent No.: US 10,548,512 B2
(45) Date of Patent: Feb. 4, 2020

(54) AUTOMATED NEAR-FALL DETECTOR

(75) Inventors: Jeffrey M. Hausdorff, Hashmonaim (IL); Nir Giladi, Tel-Aviv (IL)

(73) Assignee: The Medical Research, Infrastructure and Health Services Fund of the Tel Aviv Medical Center, Tel-Aviv (IL)

( * ) Notice: Subject to any disclaimer, the term of this patent is extended or adjusted under 35 U.S.C. 154(b) by 40 days.

(21) Appl. No.: 13/380,863

(22) PCT Filed: Jun. 24, 2010

(86) PCT No.: PCT/IL2010/000505
§ 371 (c)(1),
(2), (4) Date: Dec. 26, 2011

(87) PCT Pub. No.: WO2010/150260
PCT Pub. Date: Dec. 29, 2010

(65) Prior Publication Data
US 2012/0101411 A1    Apr. 26, 2012

Related U.S. Application Data

(60) Provisional application No. 61/219,811, filed on Jun. 24, 2009.

(51) Int. Cl.
*A61B 5/00* (2006.01)
*A61B 5/11* (2006.01)

(52) U.S. Cl.
CPC .................. *A61B 5/1117* (2013.01)

(58) Field of Classification Search
CPC ...................................................... A61B 5/00
USPC ...................................... 600/300, 587, 595
See application file for complete search history.

(56) References Cited

U.S. PATENT DOCUMENTS

| | | | |
|---|---|---|---|
| 6,201,476 B1 * | 3/2001 | Depeursinge et al. | 340/573.1 |
| 6,703,939 B2 * | 3/2004 | Lehrman et al. | 340/669 |
| 6,997,882 B1 * | 2/2006 | Parker | A61B 5/08 600/301 |
| 7,282,031 B2 * | 10/2007 | Hendrich | 600/300 |
| 8,016,776 B2 * | 9/2011 | Bourget et al. | 600/587 |
| 8,206,325 B1 * | 6/2012 | Najafi et al. | 600/595 |
| 8,284,070 B2 * | 10/2012 | Chaudhari et al. | 340/686.1 |
| 8,381,603 B2 * | 2/2013 | Peng | A61B 5/1117 600/587 |
| 8,747,336 B2 * | 6/2014 | Tran | 600/587 |
| 2001/0004234 A1 * | 6/2001 | Petelenz et al. | 340/539 |
| 2002/0008630 A1 * | 1/2002 | Lehrman et al. | 340/669 |

(Continued)

FOREIGN PATENT DOCUMENTS

| | | |
|---|---|---|
| WO | WO 2007/136677 | 11/2007 |
| WO | WO 2009/083032 | 7/2009 |
| WO | WO 2010/126878 | 11/2010 |

OTHER PUBLICATIONS

Office Action dated Aug. 26, 2013 From the Israel Patent Office Re. Application No. 217152 and Its Translation Into English.
Communication Pursuant to Article 94(3) EPC dated Oct. 4, 2012 From the European Patent Office Re. Application No. 10742909.4.
International Preliminary Report on Patentability dated Jan. 12, 2012 From the International Bureau of WIPO Re. Application No. PCT/IL2010/000505.

(Continued)

*Primary Examiner* — May A Abouelela

(57) ABSTRACT

A method of gait data collection, the method comprising collecting movement data, determining from the data a movement parameter that includes a third order derivative of position, comparing the movement parameter with a threshold value, and counting at least a near fall if the movement parameter exceeds the threshold value.

47 Claims, 7 Drawing Sheets

(56) References Cited

U.S. PATENT DOCUMENTS

| | | | |
|---|---|---|---|
| 2002/0118121 A1* | 8/2002 | Lehrman et al. | 340/870.16 |
| 2005/0182305 A1* | 8/2005 | Hendrich | 600/300 |
| 2005/0209645 A1* | 9/2005 | Heruth et al. | 607/3 |
| 2005/0240086 A1* | 10/2005 | Akay | 600/300 |
| 2006/0139166 A1* | 6/2006 | Choutier et al. | 340/539.12 |
| 2006/0241521 A1* | 10/2006 | Cohen | 600/595 |
| 2006/0270949 A1* | 11/2006 | Mathie | A61B 5/0002 600/595 |
| 2007/0038155 A1* | 2/2007 | Kelly et al. | 600/595 |
| 2007/0146145 A1* | 6/2007 | Lehrman et al. | 340/573.1 |
| 2008/0129518 A1 | 6/2008 | Carlton-Foss | |
| 2008/0214963 A1* | 9/2008 | Guillemaud et al. | 600/595 |
| 2008/0281638 A1* | 11/2008 | Weatherly et al. | 705/3 |
| 2008/0319282 A1* | 12/2008 | Tran | 600/301 |
| 2009/0060287 A1* | 3/2009 | Hyde et al. | 382/118 |
| 2009/0069724 A1* | 3/2009 | Otto et al. | 600/595 |
| 2009/0105785 A1* | 4/2009 | Wei | A61N 1/36132 607/48 |
| 2009/0137933 A1* | 5/2009 | Lieberman et al. | 600/595 |
| 2009/0221937 A1* | 9/2009 | Smith et al. | 600/595 |
| 2009/0240170 A1* | 9/2009 | Rowley | A61B 5/1117 600/595 |
| 2009/0318779 A1* | 12/2009 | Tran | 600/301 |
| 2009/0322540 A1* | 12/2009 | Richardson | A61B 5/0002 340/573.7 |
| 2010/0056957 A1* | 3/2010 | Vuillerme et al. | 600/587 |
| 2010/0217159 A1* | 8/2010 | Wukasch | A61B 5/1038 600/595 |
| 2010/0217533 A1* | 8/2010 | Nadkarni et al. | 702/19 |
| 2011/0152727 A1* | 6/2011 | Ten Kate | A61B 5/1117 600/595 |
| 2011/0190667 A1* | 8/2011 | Alwan et al. | 600/595 |
| 2012/0130286 A1* | 5/2012 | Miesel et al. | 600/595 |
| 2013/0211291 A1* | 8/2013 | Tran | 600/595 |

OTHER PUBLICATIONS

International Search Report and the Written Opinion dated Oct. 15, 2010 From the International Searching Authority Re. Application No. PCT/IL2010/000505.

Karantonis et al. "Implementation of a Real-Time Human Movement Classifier Using a Triaxial Accelerometer for Ambulatory Monitoring", IEEE Transactions on Information Technology in Biomedicine, XP002593105, 10(1): 156-167, Jan. 1, 2006.

Weiss et al. "Automated Detection of Near Falls: Algorithm Development and Preliminary Results", Biomed Central, BMC Research Notes, XP021070159, 3(62): 1-8, Mar. 5, 2010.

Communication Pursuant to Article 94(3) EPC dated Jul. 22, 2013 From the European Patent Office Re. Application No. 10742909.4.

Office Action dated Jan. 26, 2015 From the Israel Patent Office Re. Application No. 217152.

Translation dated Feb. 9, 2015 of Office Action dated Jan. 26, 2015 From the Israel Patent Office Re. Application No. 217152.

Communication Pursuant to Article 94(3) EPC dated Sep. 24, 2014 From the European Patent Office Re. Application No. 10742909.4.

Communication Pursuant to Article 94(3) EPC dated Nov. 27, 2015 From the European Patent Office Re. Application No. 10742909.4.

Office Action dated Mar. 27, 2016 From the Israel Patent Office Re. Application No. 217152 and Its Translation Into English.

Requisition by the Examiner dated Jun. 21, 2016 From the Canadian Intellectual Property Office Re. Application No. 2,765,782.

Summons to Attend Oral Proceedings Pursuant to Rule 115(1) EPC dated Sep. 28, 2016 From the European Patent Office Re. Application No. 10742909.4.

Requisition by the Examiner dated May 5, 2017 From the Canadian Intellectual Property Office Re. Application No. 2,765,782. (11 Pages).

* cited by examiner

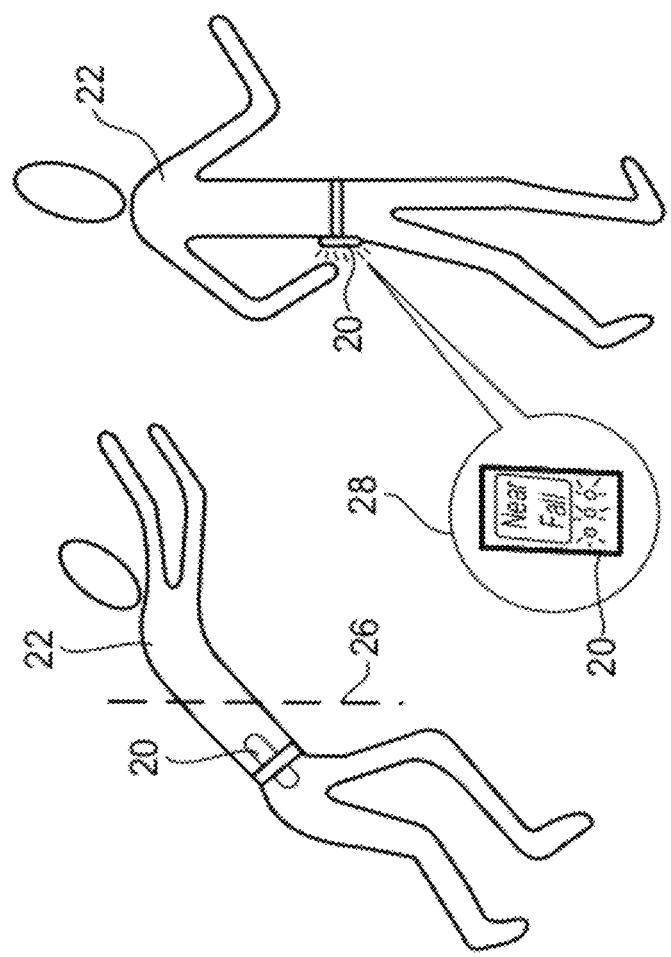
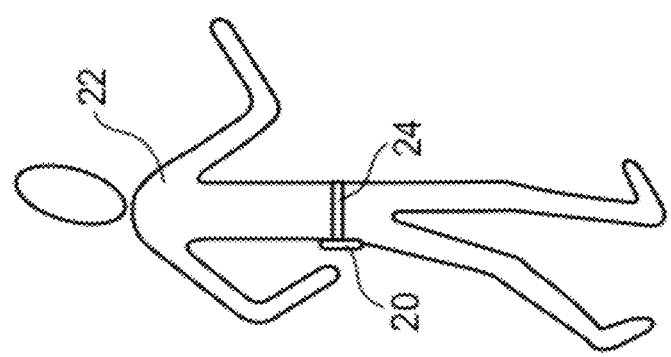
FIG. 1A  FIG. 1B  FIG. 1C

AUTOMATED NEAR-FALL DETECTOR

RELATED APPLICATIONS

This Application is a National Phase of PCT Patent Application No. PCT/IL2010/000505 having International filing date of Jun. 24, 2010, which claims the benefit of priority of U.S. Provisional Patent Application No. 61/219,811 filed on Jun. 24, 2009. The contents of the above Applications are all incorporated herein by reference.

FIELD AND BACKGROUND OF THE INVENTION

The present invention, in some embodiments thereof, relates to motion detection, and more particularly, but not exclusively, to a system useful for identifying gait or fall related motion.

A public health issue of concern is the incidence of falls, in which a person falls to the ground from an upright position while standing or walking. The problem of falls affects the elderly in general, and is of particular concern for older persons and others who have a movement disorder or other illness that affects balance and motor control, such as Parkinson's disease.

The effect of a fall on an elderly person can be particularly serious since many elderly people have weak or brittle bones, and are generally further weakened by other illnesses and the effects of aging. In some cases a fall causes the death of a person, either at the time of the fall or indirectly as a result of the injuries sustained. The type of injuries commonly experienced may include one or more of: a broken or fractured hip and other bones, head injuries, internal and external bleeding, and soft tissue and skin damage. The patient will most likely suffer a great deal of pain and may require hospitalization. In addition, he or she may face the prospect of long term or permanent loss of mobility, since their age and condition may mean that the injuries will take a long time to heal or may never heal completely. The patient may be plagued by fear of a recurrence, so that their mobility and confidence is further compromised. Accordingly, even if death is avoided, the injuries suffered from a fall can be devastating to the person's physical and mental well-being.

Various systems have been proposed to automatically identify falls, so that an action can be triggered to help alleviate the damage caused by the fall. For example, upon detecting that a fall has occurred, a system could notify a relative or doctor to check up on the patient. Dinh et al. in "A Fall Detection and Near-Fall Data Collection System" (Microsystems and Nanoelectronics Research Conference (MNRC), October 2008) describe a wearable device containing a 3-axis accelerometer, a 2-axis gyroscope, and a heart beat detection circuit. Data collected from the sensors is beamed wirelessly to a receiver connected to a computer. The researchers observed that combining the accelerometer data with the gyroscope data produced good results in identifying whether a fall had occurred.

Bourke et al. in "Distinguishing Falls from Normal ADL using Vertical Velocity Profiles", (IEEE Conference on Engineering in Medicine and Biology, August 2007) observe that a single threshold applied to the vertical velocity profile of the trunk may distinguish falls from activities of daily living (ADL).

In another paper, Wu and Xue in "Portable Preimpact Fall Detector With Inertial Sensors" (IEEE Transactions on Neural Systems and Rehabilitation Engineering, April 2008), describe a portable preimpact fall detector that detects a pending fall at its inception, so that an inflatable hip protector can be triggered in time to break the fall. The detector was equipped with an orientation or inertial sensor that included triaxial accelerometers and triaxial angular rate sensors, and used a detection algorithm based on the inertial frame velocity profile of the body. In particular, the inertial frame vertical velocity magnitude was measured and compared to a threshold value to identify a fall. The system was tested in a variety of activities to determine the threshold level of inertial frame vertical velocity magnitude.

SUMMARY OF THE INVENTION

An aspect of some embodiments of the invention relates to detection of gait irregularity and/or of near fall.

In an exemplary embodiment of the invention, a near fall is characterized based on its vertical acceleration profile, for example, the rate of change of vertical acceleration being above a threshold. Optionally, a comparison to a threshold uses inexact methods, for example fuzzy logic. Optionally or alternatively, the comparison is of a function of acceleration to a function of the threshold. Optionally, the threshold is dynamic, for example, as a function of context of the gait and/or of recent movement parameters.

In some exemplary embodiments of the invention, gait irregularity is characterized based on vertical acceleration. Typically, corresponding to gait's steps movements, movement's acceleration signal exhibits a generally cyclic pattern with peaks. In some embodiments, irregularity is determined when the periods of the cycles (e.g. between peaks) vary above a threshold. In some embodiments, the irregularity is determined when the shape of the cycles vary above a threshold, where the variability of the shape is determined, for example, by variations in cross-correlation between the cycles. In some embodiments, the irregularity is determined by a frequency spread of the acceleration signal, such as obtained with a Fourier transform.

Optionally, a comparison to a threshold uses inexact methods, for example fuzzy logic. Optionally or alternatively, the comparison is of a function of acceleration to a function of the threshold. Optionally, the threshold is dynamic, for example, as a function of context of the gait and/or of recent movement parameters.

In some embodiments, a combination of two or more of the methods, i.e. cycles time, cycles shape and frequency spread, is used to determine irregularity.

In some embodiments, the irregularity is checked along a certain or determined time. Optionally, the irregularity is checked within a moving window of a certain or determined time.

Alternatively or additionally to evaluation of near fall and/or gait irregularity by parameters or values derived from the acceleration, in some exemplary embodiments of the invention determination of near fall and/or gait irregularity is based on the waveform of the acceleration (or other movement signals).

In some embodiments, the waveform of gait acceleration over a certain period is evaluated against a reference waveform or library of waveforms of gait acceleration, and near fall and/or gait irregularity is determined or classified according to a degree of matching or mismatching with the reference waveform(s).

In some embodiments, the waveform of a subject is matched against a reference waveform by methods of pattern matching such as correlation or cross-correlation or wavelet matching or machine learning (e.g. neural networks) or any combination of methods of the art.

In some exemplary embodiments of the invention, a derivative of the accelerations is used to determine near fall and/or gait irregularity. Optionally, other parameters such as angular velocity or tilt are used.

An aspect of some embodiments of the invention relates to gait regulation assistance. In some embodiments, irregularity in gait is detected, such as described above. Responsive to a determined gait irregularity of a person, the person is prompted, such as by audio message or tactile incitement, to adjust and/or stabilize the gait (cuing signals).

An aspect of some embodiments of the invention relates to enhancing a Timed Up and Go (TUG) test to assess the tendency of a person to fall (persons prone to fall). In some embodiments, the enhancement is based on the rate of change of position during sitting or rising (jerks), such as a time derivative of the vertical acceleration. In some embodiments, the tendency to falling is assessed when the rate of change of the acceleration is above a threshold. In some embodiments, the threshold is based on the rate of change of acceleration of healthy person or persons. Optionally or additionally, the threshold is based on the physiological state of the person being assessed, such as neurological disorder.

There is provided in accordance with an exemplary embodiment of the invention, a method of gait data collection, the method comprising:

A method of gait data collection, the method comprising:
collecting movement data, and
determining from said data at least one irregularity of the gait.

In some embodiments, an irregularity comprises a near fall.

In some embodiments, an irregularity comprises a fall.

In some embodiments, determining comprises determining from said data a movement parameter that includes a third order derivative of position, and counting at least a near fall based on said movement parameter.

In some embodiments, determining comprises matching the pattern with respect to time of the movement data with a reference pattern.

In some embodiments, the reference pattern represents proper gait pattern.

In some embodiments, the reference pattern represents improper gait pattern.

In some embodiments, the reference pattern represents a gait pattern exhibiting at least one near fall.

In some embodiments, the matching classified the data as exhibiting fall, near fall or lack thereof.

In some embodiments, wherein the matching comprises at least one of correlation, cross-correlation, wavelets matching or neural networks or a combination thereof.

In an exemplary embodiment of the invention, the method comprises comparing said movement parameter with a threshold value to identify a near fall.

In an exemplary embodiment of the invention, said movement parameter comprises a difference between a maximum acceleration derivative and a minimum acceleration derivative. Optionally, said movement parameter relates to movement in substantially a vertical direction.

In an exemplary embodiment of the invention,
determining from said data further includes determining a second movement parameter,
comparing said movement parameter further includes comparing said second movement parameter with a second threshold value, and
counting at least a near fall comprises counting at least a near fall if said movement parameter exceeds said threshold value and said second movement parameter exceeds said second threshold value.

In an exemplary embodiment of the invention, said second movement parameter includes a second order derivative of position. Optionally or alternatively, said movement parameter and said second movement parameter relate to movement in substantially a vertical direction.

In an exemplary embodiment of the invention, said threshold value is a predetermined value.

In an exemplary embodiment of the invention, said threshold value is a continuously updated function of said movement parameter. Optionally, said function is a mean of said movement parameter plus a multiple of a standard deviation of said movement parameter.

In an exemplary embodiment of the invention, determining a movement parameter comprises collecting acceleration data and taking a derivative of said acceleration data with respect to time.

In an exemplary embodiment of the invention, determining a movement parameter comprises collecting velocity data and taking a second order derivative of said velocity data with respect to time.

In an exemplary embodiment of the invention, determining a movement parameter comprises collecting position data and taking a third order derivative of said position data with respect to time.

In an exemplary embodiment of the invention, said count of at least a near fall provides a quantitative measure of effectiveness of therapeutic interventions.

There is provided in accordance with an exemplary embodiment of the invention, a method of gait data collection, the method comprising:

collecting movement data,
determining from said data a plurality of movement parameters, each of said movement parameters including at least one of a second order derivative of position and a third order derivative of position,
comparing each of said movement parameters with an associated threshold value, and
counting at least a near fall if a predetermined combination of movement parameters from said plurality of movement parameters exceeds their associated threshold value.

There is provided in accordance with an exemplary embodiment of the invention, a method of gait data collection, the method comprising:

collecting movement data,
extracting from said movement data an indicator indicating a loss of control,
counting at least a near fall if said indicator indicates said loss of control.

There is provided in accordance with an exemplary embodiment of the invention, a device to detect falling body movement, the device comprising:

a sensor operatively connected to said body and responsive to movement of said body, and
a processor to receive movement data from said sensor and to process said movement data to identify events that are at least near falls.

In an exemplary embodiment of the invention, said processor is configured to log a record of events that are at least near falls. Optionally or alternatively, said sensor is responsive to movement of said body in substantially a vertical direction. Optionally or alternatively, said sensor is responsive to acceleration of said body.

In an exemplary embodiment of the invention, the device includes a user interface to communicate with a user of said device.

In an exemplary embodiment of the invention, said sensor and said processor are enclosed in a housing.

In an exemplary embodiment of the invention, said processor is located remote from said sensor.

In an exemplary embodiment of the invention, the device includes a radio transmitter operatively connected to said sensor and a radio receiver operatively connected to said processor, wherein said transmitter and said receiver are configured to enable said processor to receive movement data from said sensor in real time.

There is provided in accordance with an exemplary embodiment of the invention a method for assisting a person's gait, comprising:

(a) detecting, based on time derivation of gait movements, irregularity in the gait; and (b) providing gait regulating cueing signals.

There is provided in accordance with an exemplary embodiment of the invention an apparatus for assisting a person's gait, comprising:

(a) a sensor operatively connected to the person and responsive to movement of said person;

(b) a processor adapted to receive movement data from said sensor and to process said movement data to detect irregularity in the movement; and (c) at least one device operable to provide cuing signals responsive to detected irregularity.

In some embodiments, the signals are at least one of audible, tactile or visual.

There is provided in accordance with an exemplary embodiment of the invention a method for augmenting a Timed Up and Go test, comprising:

(a) determining rate of change of acceleration of movement about at least one of seating or rising; and (b) screening, based on the rate of change of the acceleration, a tendency to fall.

In some embodiments, the screening is determined of a rate larger than that of a healthy person.

In some embodiments, the screening is determined when the rate of the acceleration of a sitting movement is about 1 g/sec In some embodiments, the screening is determined when the rate of the acceleration of a rising movement is about 2 g/sec Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A, 1B, and 1C are schematic views of a person walking, having a near fall, and recovering to resume walking, respectively, while wearing an automated near-fall detector, in accordance with an embodiment of the invention;

DESCRIPTION OF SPECIFIC EMBODIMENTS OF THE INVENTION

Figure 2A:
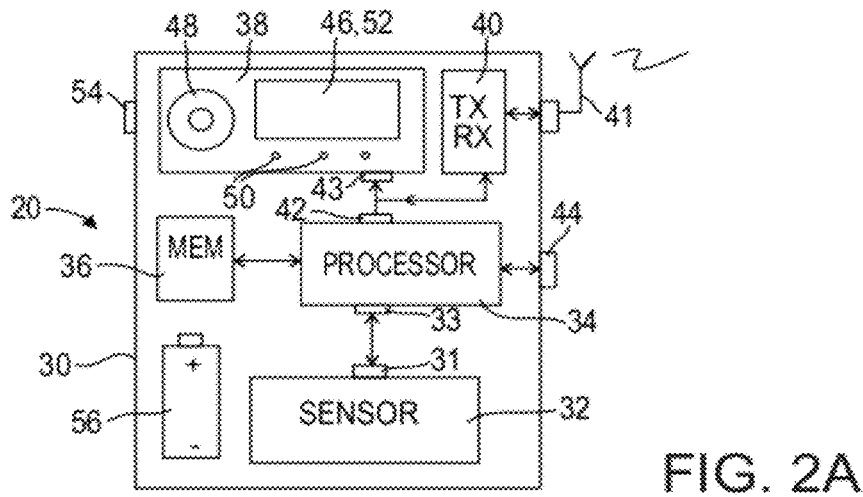
FIGS. 2A, 2B, and 2C are schematic views of the automated near-fall detector of FIG. 1, in accordance with several embodiments of the invention.

The present invention, in some embodiments thereof, relates to motion detection, and more particularly, but not exclusively, to a system useful for identifying gait or fall related motion.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

In an exemplary embodiment of the invention, a near fall is characterized based on its vertical acceleration profile, for example, the rate of change of vertical acceleration being above a threshold. Optionally, a comparison to a threshold uses inexact methods, for example fuzzy logic. Optionally or alternatively, the comparison is of a function of acceleration to a function of the threshold. Optionally, the threshold is dynamic, for example, as a function of context of the gait and/or of recent movement parameters.

In some exemplary embodiments of the invention, gait irregularity is characterized based on vertical acceleration. Typically, corresponding to gait's steps movements, movement's acceleration signal exhibits a generally cyclic pattern with peaks. In some embodiments, irregularity is determined when the periods of the cycles (e.g. between peaks) vary above a threshold. In some embodiments, the irregularity is determined when the shape of the cycles vary above a threshold, where the variability of the shape is determined, for example, by variations in cross-correlation between the cycles. In some embodiments, the irregularity is determined by a frequency spread of the acceleration signal, such as obtained with a Fourier transform.

Optionally, a comparison to a threshold uses inexact methods, for example fuzzy logic. Optionally or alternatively, the comparison is of a function of acceleration to a function of the threshold. Optionally, the threshold is dynamic, for example, as a function of context of the gait and/or of recent movement parameters.

In some embodiments, a combination of two or more of the methods, i.e. cycles time, cycles shape and frequency spread, is used to determine irregularity.

In some embodiments, the irregularity is checked along a certain or determined time. Optionally, the irregularity is checked within a moving window of a certain or determined time.

Alternatively or additionally to evaluation of near fall and/or gait irregularity by parameters or values related to the size of the acceleration or other movement signal (i.e., above or below a threshold), in some exemplary embodiments of the invention determination of near fall and/or gait irregularity is based on the waveform of the acceleration (or movement signal).

In some embodiments, the waveform of gait acceleration over a certain period is evaluated against a reference waveform(s) of gait acceleration, and near fall and/or gait irregularity is determined or classified according to a degree of matching or mismatching with the reference waveform. In some embodiments, the classification comprises a fall or near fall event or the lack thereof.

In some embodiments, the waveform of acceleration of the gait of a subject is matched against a reference waveform by methods of pattern matching such as correlation or cross-correlation or wavelet matching or machine learning (e.g. neural networks) or any combination of methods of the art. Optionally the determination or classification of gait irregularity and/or near fall by matching methods is augments by other methods such as fuzzy logic.

When a subject's waveform sufficiently deviates from a reference signal representing a proper gait, the subject is determined to exhibit irregular gait. Optionally, by features matching between the waveforms a near fall is determined if characteristic features are different between the waveforms.

When a subject's waveform sufficiently matches a reference signal representing an improper gait, the subject is determined to exhibit irregular gait. Optionally, when the subject's waveform sufficiently matches a waveform with near fall events, the subject is determined to exhibit near fall behavior. Optionally, by features matching between the waveforms a near fall is determined if characteristic features are similar between the waveforms.

For example, the acceleration waveform of a subject is matched against a waveform representing a healthy gait, and if the waveforms deviated above a threshold the subject's gait is determined to be irregular. Optionally, features of the waveforms are matched and based on dissimilarities such as missing or different features between the waveforms, the subject's gait is determined to exhibit near fall behavior.

As another example, the acceleration waveform of a subject is matched against a waveform representing a person having improper gait. If, based on a threshold or other measures, the waveforms are sufficiently close and/or exhibit similar features the subject's gait is determined to be irregular or having near fall characteristics. Optionally, features of the waveforms are matched and according to some measures, such as missing or different features between the waveforms, the subject's gait is determined to exhibit near fall behavior.

In some embodiments, a 'healthy' or 'proper' reference waveform is based on the gait of healthy persons, optionally of about the age of the subject being evaluated. For example, acceleration waveforms of healthy persons are collected and combined, such as by scaling and averaging or by any other methods, to provide a representative waveform of proper or regular gait. Optionally, the representative waveform is based, at least partially, on the gait acceleration of other neurologically diseased while they exhibit regular gait. Optionally, the representative waveform is based, at least partially, on synthetic waveform computed to represent a proper gait.

In some embodiments, an 'ill' or 'improper' reference waveform is based on the gait of neurologically diseased persons, optionally of about the age and/or disorder of the subject being evaluated. For example, acceleration waveforms of persons exhibiting irregular or disordered or near fall behavior are collected and combined, such as by scaling and averaging or by any other methods, to provide a representative waveform of improper gait. Optionally, the representative waveform is based, at least partially, on the gait acceleration of other neurologically diseased while they exhibit irregular gait. Optionally, the representative waveform is based, at least partially, on synthetic waveform computed to represent an improper gait.

In some embodiments, in order to improve or refine the evaluation of a subject's waveform, the waveform is matched against a plurality of reference waveforms, either proper and/or improper waveforms. For example, the subject's waveform is matched against both proper and improper references and the irregularity or near fall characteristics are determined by a combination of the matching results.

In some embodiments, the representative waveforms are updated from time to time to form a library or repository of reference waveforms.

In some exemplary embodiments of the invention a derivative of the accelerations are used to determine near fall and/or gait irregularity. Optionally, other parameters such as angular velocity or tilt are used such as to refine the determination of fall and/or gait irregularity.

In some embodiments, the presence or absence of a near fall or other gait irregularity is made by combining methods based on pattern recognition of the waveforms with those that are based on threshholding of the acceleration jerk or other derived movement parameters.

In some embodiments, irregularity in gait is detected, such as described above. Responsive to a determined gait irregularity of a person, the person is prompted, such as by audio message or tactile incitement, to adjust and/or stabilize the gait (cuing signals).

In some embodiments, a Timed Up and Go (TUG) test to assess the tendency of a person to fall (persons prone to fall) is enhanced. In some embodiments, the enhancement is based on the rate of change of position during sitting or rising (jerks), such as a time derivative of the vertical acceleration. In some embodiments, the tendency to falling is assessed when the rate of change of the acceleration is above a threshold. In some embodiments, the threshold is based on the rate of change of acceleration of healthy person or persons. Optionally or additionally, the threshold is based on the physiological state of the person being assessed, such as neurological disorder.

1. Overview

FIGS. 1A, 1B, and 1C show a near fall detector device 20, according to an embodiment of the invention, in a typical application being used by a walking person 22. Person 22 may be a man or woman of any age and of any physical condition. In this example near fall detector 20 is a device attached to a belt 24 worn by person 22. As will be discussed in greater detail below, near fall detector 20 optionally uses signal processing methods to monitor the quality of a walking person's gait or ambulatory movement, and responds or records in some fashion in the event that the person's walk is interrupted by a near fall or a real fall. Optionally, detector 20 is also capable of detecting a fall or near fall that may be experienced by a person that is standing or sitting.

In FIG. 1A person 22 is shown walking in a normal fashion. At some later point in time, as shown in FIG. 1B, person 22 experiences a near fall. The near fall, also called a stumble or misstep, is a momentary loss of balance by the person from which the person recovers. By contrast, in a real or actual fall (or just "fall") the person does not recover and continues to fall until he or she comes to rest on the ground, floor, or other lower level. FIG. 1B illustrates some characteristics of an example of a near fall. As may be seen, the person's legs have slipped so they are no longer directly underneath, and accordingly the person's center of gravity 26 has moved off center so that the person experiences a sensation of loss of balance. As most people may relate, the person's arms thrust out to compensate in an effort to recover balance and avoid falling. In this example person 22 is successful at avoiding the fall, and is shown in FIG. 1C at a later point in time resuming his or her walk. Near fall detector 20 however has detected the incident shown in FIG. 1B. This is indicated, by way of example, in the enlarged representation of the detector in inset 28 in FIG. 1C, which shows detector 20 displaying the words "Near Fall". In other examples, detector 20 might log a record of the incident and not display anything, or detector 20 might query the user to confirm the near fall.

The near fall illustrated in FIG. 1B could occur in any direction, have a degree of magnitude or force behind it, and be due to any cause. For example, the near fall could be in a forward direction (as shown in the figure), as might occur due to tripping. Other types of near falls include, for example, a backward near fall caused by a slippery floor, or a sideways near fall caused by a misstep. The person might also have a near fall directed straight down, for example due to fainting. Near falls may be caused by external circumstances, such as an unexpected obstacle or slippery surface, or by circumstances internal to the person, such as by fainting, general weakness, or a movement disorder. In many cases the near fall is caused by a combination of the two. For example, an obstacle may be encountered that a healthy person would easily avoid, but that precipitates a near fall in an older person with poor eyesight and a slow reaction time. In an exemplary embodiment of the invention, near fall detection is practiced in clinical/diagnostic settings, where a patient is given a task, such as an obstacle course, and his performance thereon monitored.

In addition to detecting the incident of a near fall, near fall detector 20, in some embodiments of the invention, may also detect the magnitude and/or direction of the near fall. Further, as will be discussed in greater detail below, near fall detector 20 in some embodiments of the invention performs gait data collection and/or includes an algorithm configured to detect the occurrence of actual falls as well as near falls.

The inventors have realized that many people who have experienced actual falls, or that are prone to falling, may in fact only fall a relatively small number of times. This does not detract from the seriousness of the problem, since all it takes is one bad fall to seriously injure a person. However, it does suggest that for such people it can be difficult to collect meaningful data to prevent future falls, especially if their memory is faulty and/or if interrogation occurs at a time after such an event. The inventors have further observed that people at risk of falling often have multiple near falls for every actual fall that they experience, and also prior to their falling for the first time. In an exemplary embodiment of the invention, the detection of near falls provides insight into a person's condition that may assist in the diagnosis and prevention of subsequent real falls by that person.

As discussed in greater detail below, near fall data can provide quantifiable parameters whose value can be used to better assess the person at risk. Additionally, when combined with data on a person's actual falls (which as noted can also be obtained from detector 20 of some embodiments of the present invention), a diagnostician can obtain a ratio (or other relationship) of actual falls to near falls and acquire a more complete picture of the person's condition. Through a review of the pattern of near fall frequency and optionally other parameters such as magnitude and direction of the near falls that might precede a full fall, near fall detector 20, in an embodiment of the invention, may be useful to alert a person and/or the person's physician that the person is at risk of falling. The person may then respond by wearing protective padding r other safety equipment, for example, or by taking other suitable precautions that prevent a fall from happening that would otherwise have occurred. Near fall data may also provide a quantitative measure that can be used to evaluate the effectiveness of therapeutic interventions.

Near fall detector 20 of the present invention, in some embodiments, can be configured to automatically record and/or report the number of instances of near falls, as well as details of each near fall such as one or more of the date and time at which it occurred, its magnitude, direction, its location and/or movements before or after the fall (e.g., indicating stair climbing, fast walking or other gait, task and/or physiological characteristics). This feature of automatic self-reporting represents an improvement in accuracy over self-reporting of near fall instances by the person. Self-reporting can be highly unreliable because it is subjective in nature, relying on the patient's memory and motivation, and/or lacks sensitivity, in that a patient might not recognize that an experience was in fact a near fall (particularly if its magnitude was low). Self-reporting also usually requires a long observation period, such as six months or a year. Optionally, the systems described herein, while usable for long periods, can be used for short periods, such as 1-10 hours, 1-10 days or 1-10 weeks, or intermediate periods.

As will be discussed in greater detail below, near fall and actual fall detection in some embodiments of the invention is measured based on acceleration of person 22. Some embodiments are based on the inventive realization that whereas regular walking is a controlled form of movement that involves a consistent level of acceleration, when there is a fall there is a loss of control resulting in a much higher level of acceleration. Movement data obtained for near falls and other parameters can be used to construct a "gait acceleration profile" that is particularly configured to the movement or gait characteristics of the person. It is hypothesized, without being limited to any particular hypothesis, that one or more parameters of the person's gait acceleration profile constitute a useful measure or indicator of loss of control by person 22. Alternatively, one or more parameters of the gait acceleration profile may be viewed as an indicator of over-control by person 22, since in recovering from a near fall and avoiding a real fall, person 22 has made a successful attempt to regain control.

In some embodiments of the invention, detector 20 counts both near falls and actual falls. Data relating to both experiences comprise the gait acceleration profile of the person. The two types of events may be lumped together, or alternatively, upon further analysis of the data, instances of near falls may be separated from instances of actual falls. Optionally, falls are detected based on the sudden deceleration at the end of a fall, or based on the time of the fall and/or a time integral of velocity or acceleration which indicates vertical distance moved of the sensors.

In some exemplary embodiments of the invention, detector 20 is configured to detect gait irregularity. Optionally, detector 20 is configured to detect gait irregularity in addition to near fall detection. Optionally or alternatively, detector 20, or a variation thereof, is configured to detect gait irregularity irrespective or instead of near fall.

In some embodiments, gait irregularity detection is based on vertical acceleration. Typically, corresponding to gait's steps, the acceleration signal exhibits a generally cyclic pattern with characteristic peaks. In some embodiments, irregularity is determined when the periods of the cycles (e.g. between peaks) vary above a threshold. Optionally or additionally, the irregularity is determined when the shape of the cycles vary above a threshold, where the variability of the shape is determined, for example, by cross-correlation. Optionally or additionally, the irregularity is determined by a frequency spread of the acceleration signal, obtained for example, with a Fourier transform.

In some embodiments, detector 20 is configured to assist in regulating a person's gait. Responsive to a detected gait irregularity of a person, the person is prompted by cuing signals, such as audio message or vibration, to adjust and/or stabilize the gait.

In some embodiments, detector 20 is configured to enhance a Timed Up and Go (TUG) test to assess the tendency of a person to fall. In some embodiments, the enhancement is based on time derivative of the vertical acceleration. In some embodiments, a tendency to falling is detected when the rate of change of the acceleration is above a threshold. In some embodiments, the threshold is based on the rate of change of acceleration of healthy person or persons. Optionally or additionally, the threshold is based on the physiological state of the person being assessed, such as neurological disorder.

2. Exemplary Structure

Figure 2B:
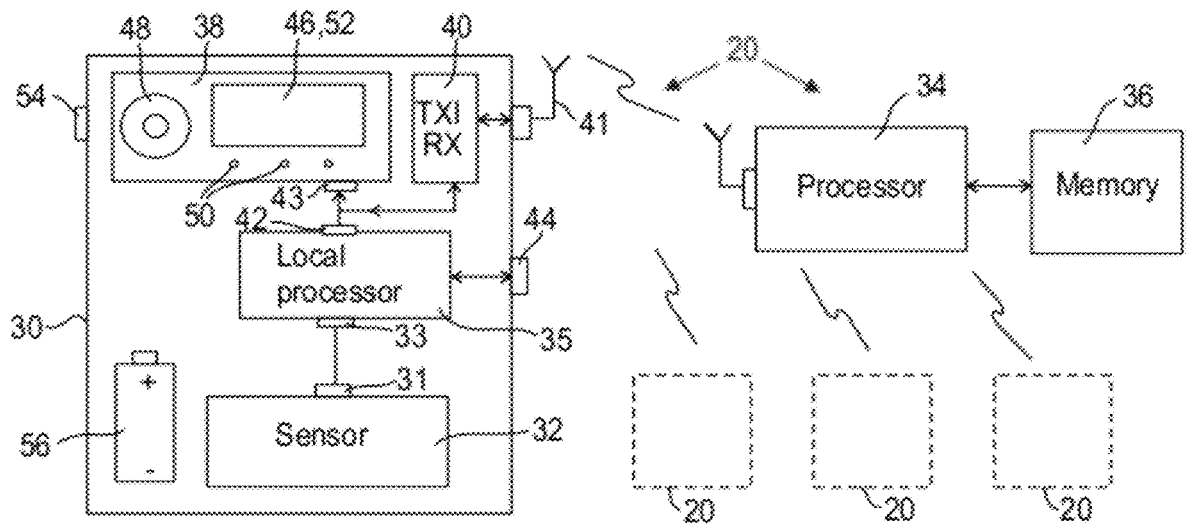
Figure 2C:
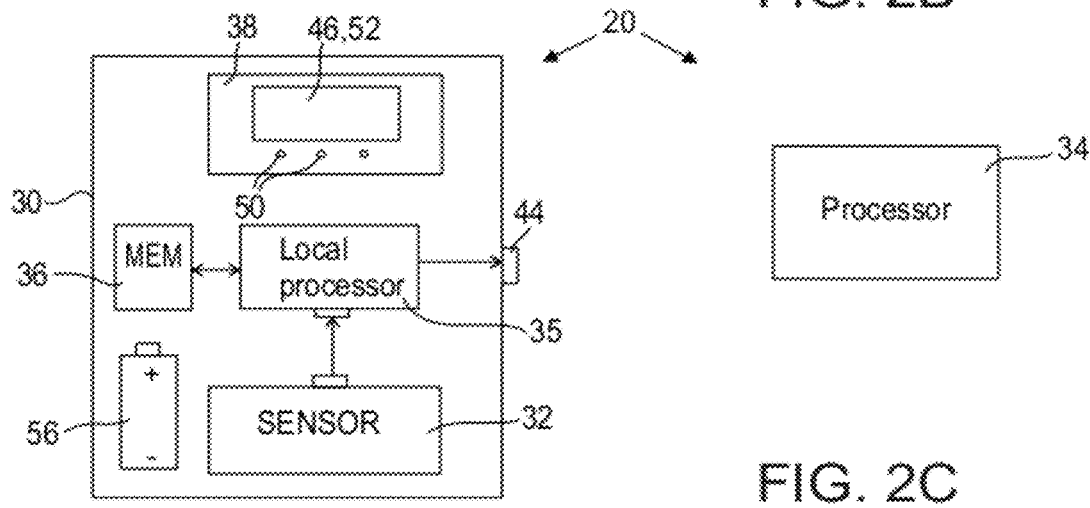

FIGS. 2A, 2B, and 2C shows the component elements of three exemplary embodiments of near fall detector 20.

The embodiment of FIG. 2A is a self-contained device, in which all of the elements are contained in a common housing or casing 30. As discussed in greater detail below, this embodiment includes features that provide real-time feedback to the user. Accordingly, this embodiment could be used as near fall detector 20 in the example of FIG. 1.

As shown in FIG. 2A, near fall detector 20 includes a sensor 32. This component may be any sensor configured to measure an aspect of movement such as a change of acceleration, velocity, or position. An accelerometer, which is a type of sensor that measures acceleration directly relative to freefall, may be used for sensor 32 in some embodiments. Accelerometers are convenient to use because they are widely available and inexpensive relative to specialized acceleration measuring devices. In addition, as will be discussed in greater detail below, measuring acceleration directly provides the benefit of reducing the processing burden on the device, as compared with a sensor that measures position or velocity. The tolerance or sensitivity of sensor 32 should be about 800 mV/g or better. The sampling frequency of sensor 32 may be about 100 Hz, and optionally is not less than about 60 Hz in order to obtain adequate results. A sampling rate that is too low may adversely affect sensing quality.

A parameter of sensor 32 is the number of axes in space in which the sensor takes its measurements. Tri-axial sensors 32 are configured to measure in all three orthogonal orientations in space, specifically the vertical, medio-lateral, and anterior-posterior directions. A single axis sensor may measure along one axis only, such as in the vertical direction, and a bi-axial sensor measures in two directions. Sensor 32 of the present invention may be a tri-axial sensor in all embodiments, but may also be a bi-axial or single axis sensor in some embodiments, as long as one of the axes of measurement is the vertical axis. In some cases a bi-axial or single axis sensor may be less expensive than a tri-axial sensor. However, the use of tri-axial sensors may enhance detection accuracy and reliability, and may also provide the monitoring physician with additional information about the direction and nature of any near falls. An example of an accelerometer that may be used for sensor 32 is the Dynaport, manufactured by the McRoberts company of the Netherlands. If a single axis accelerometer is used, detector 20 optionally includes an indicator (e.g., an arrow) to show which part of detector should be aimed in a certain direction (e.g., up).

In this embodiment sensor 32 transmits the measured movement data to a processor 34. As shown, the transmission is made through a sensor output port 31 on sensor 32, which connects directly to a processor input port 33 of processor 34.

Processor 34 may be a numeric processor, computer, or related electronic component such as an application specific integrated circuit (ASIC), electronic circuit, micro-controller, or microprocessor capable of processing the raw movement data measured by sensor 32. Optionally, the speed of processing, such as a speed of a computation cycle of measurement or measurements of sensor 32, is at least that of the sampling frequency of sensor 32. In some embodiments processor 34 records acceleration values and calculates derivatives or other parameters of acceleration. Processor 34 further includes and/or is coupled with software (not shown) that directs operation of the processor. Internal memory (not shown) may optionally be included in and/or is coupled with processor 34 to store logged and derived acceleration values, and/or other numerical values calculated by the software. Alternatively or additionally, processor 34 may connect with a separate memory module 36 to store these values. In some embodiments, processor 34 is further configured to control some or all aspects of a user interface 38 and/or a radio transmitter or receiver or combined transmitter/receiver ("transceiver") 40. Connection with these elements may be made in some embodiments through a processor output port 42 and a user interface input port 43.

Processor 34 may also connect with an external device such as a computer through an optional external interface port 44. This connection may enable processor 34 to transfer data to the external computer and/or to receive a software program, software updates, or other inputs, for example, by a physical connection (e.g. wired) and/or wirelessly such as using a Bluetooth or a Wifi or cellular connection. In some embodiments, external port 44 may be a USB port or other industry standard connection. For additional flexibility, external port 44 may comprise two or more such ports rather than just one.

After person 22 has used the device for a given period of time, a record of the person's near fall and other gait related data is optionally stored in the device (optionally as it occurs). This processed data may be provided to the person's doctor by connecting device 20 through port 44 into a corresponding port, such as a USB port, of a computer. The data may then be transferred between devices in the manner well known in the art. In practice, person 22 may hand device 20 to the doctor or doctor's staff when visiting the doctor for an appointment, and the information may then be transferred to the doctor's computer directly. Alternatively, person 22 might transfer the information to his or her own computer and then email it to the doctor. Alternatively, the information might be sent wirelessly directly or indirectly from device 20 to the doctor's computer or another location, for example, by email. Another embodiment includes real-time transfer of the data as it is processed for online monitoring. In some embodiments, the memory is or comprises a removable card such as an SD card. Data on the card can be read by a card reader, and the data is optionally transferred to a computer and/or for archiving such as on hard disk or CD or DVD.

User interface 38 is an element of near fall detector 20 configured, in some embodiments, to provide information to the user or person 22 and/or to receive information from the user. The information may be in any convenient format such as visual, audio, and/or touch, and may be configured to meet the particular needs of the user. For example, in some embodiments user interface 38 may emphasize audio-based elements rather than visual elements, to better meet the needs of elderly users whose sight is weak.

User interface 38 may optionally include information output elements such as a visual display screen 46 capable of displaying alphanumeric and/or graphical messages, a speaker 48, and/or alarm lights 50. Optional user input elements include a touchscreen 52, microphone 54, keypad, and touchpad (not shown). In some embodiments, user interface 38 may include a camera and/or a video recorder.

In some embodiments, visual display screen 46 may also include the functionality of touchscreen 52, and accordingly comprise a means for both displaying information to the user and receiving information from the user. Visual display screens 46 based on liquid crystal technology (LCD) may be used due to their readability and low power requirements, but other types of display and/or touchscreen technologies may also be used.

As noted, near fall detector 20 optionally includes wireless transceiver 40. In a handheld device, transceiver 40 in some embodiments will operate at relatively high frequencies such as from about 100 MHz to 2 GHz, this may allow a device to be made smaller. Transceiver 40 optionally connects to processor 34 through processor output port 42, and may include a transponder (not shown), antenna 41, and other radio frequency components required to maintain wireless communication. In some embodiments transceiver 40 may comprise a radio and antenna such as that used in a cellular telephone or, in other embodiments, components of the type used in a computer standard Bluetooth interface.

In order to power the elements of near fall detector 20, an energy source such as a battery 56 may be used. In some embodiments battery 56 is a light weight battery that provides power for an extended number of hours, or even several days or weeks. In this way, near fall detector may be used for the greater part of a day, and enable a meaningful amount of data to be gathered. In some embodiments battery 56 is a lithium ion battery, but other battery types, for example, rechargeable or one-time may be used as well.

The various optional elements of user interface 38, along with transceiver 40, may be combined to provide a range of responses that assist person 22 in the event of a near fall or a fall. For example, upon detecting a near fall or fall, speaker 48 could emit an audible beep and then deliver a message in the form of a human voice asking if the person is ok, and requesting person 22 to press a button on the device or screen for confirmation. Alternatively, the message could be a visual one on display screen 46. If the user signals that he or she is ok no further action need be taken. If the user suggests otherwise or does not respond within a predetermined time, near fall detector 20 may be programmed to automatically send an email, page, or text message to a family member or doctor to alert them that person 22 fell or has almost fallen and needs assistance. An optional geographical position system (gps) in near fall detector 20 may automatically inform the doctor of the location of the person. In some embodiments, the device could automatically dial the doctor's phone number to enable direct voice communication.

In some embodiments, near fall detector 20 could be programmed to engage person 22 in a dialogue, to obtain more precise information. Person 22 could respond in a variety of ways, such as by keyboard, touchscreen, or by speaking into microphone 54. Sample questions from such a dialogue may be, for example, "did you fall?", "are you ok?", "where are you?", "do you need help?", and "would you like to call your doctor/spouse?". The device might also be used to record a voice or video message by person 22 and forward the message to the assisting party.

Housing or casing 30 is optionally sized and/or shaped sufficiently large to enclose the various components. Internal elements such as sensor 32 and processor 34 are optionally shielded from the elements, and/or user interface elements such as a keyboard, visual display screen 46, if present, are optionally easy to access. Housing 30 is optionally made of a rigid and durable plastic, but other materials that are light and strong, such as aluminum, may also be used. Optionally, housing 30 includes a clip (not shown) for convenient attachment to belt 24 or other article of clothing. If sensor 32 requires a particular orientation when the device is mounted on belt 24 in order to operate effectively, visual or audio feedback may be provided by the appropriate elements of user interface 38 to assist person 22.

Near fall detector 20 in some embodiments of the invention may comprise a dedicated device having as its only or primary function the detection of near falls and actual falls. In some embodiments, near fall detector 20 may be incorporated into other types of electronic devices used primarily for other purposes unrelated to fall detection. Examples of such devices include cellphones, pagers, portable media players, mobile Internet devices, and the like. This configuration may be more convenient for the user as it reduces the number of devices to be carried, and may also reduce the risk that the user will forget to take near fall detector 20.

In some of these embodiments all or most of the hardware elements may already be available as part of the function of the device. For example, some cellphones known as "smartphones" and even some "regular" cellular telephones and PDAs include relatively powerful computer processors, accelerometers, visual display screens and speakers, wireless telephone and data communication hardware, and the like. Accordingly, some smartphones may only require the addition of specialized software to become configured as near fall detector 20, according to some embodiments of the invention. In some instances the smartphones may need other modification such as the addition of memory module 36 and/or adding of a sensors, optionally with wired or wireless linking to the smartphone.

In some embodiments of the invention, near fall detector 20 may be incorporated into a medical device implanted in (or carried by) the user's body for medical purposes, such as a brain pacemaker for example. Other examples of such implanted devices include heart pacemakers, prosthetic hips, and implanted pumps for chronic pain. Similar to smartphones, some of these devices may already include a processor or accelerometer and accordingly may only require software to function as near fall detector 20, according to some embodiments of the invention.

Turning now to FIG. 2B, in this embodiment processor 34 is separated from the portable part of device 20 contained in housing 30 and placed at a remote location. In an exemplary embodiment of the invention, remote processor 34 receives movement data from sensor 32 in real time (e.g. sufficiently fast to detect a near fall) through transceiver 40, and communicates with and controls user interface 38 through wireless communication. Remote processor 34 otherwise functions similarly to integrated processor 34 of the embodiment of FIG. 2A, in that it processes and monitors near falls and communicates with person 22 and doctors or other assisting parties. Since this embodiment performs data analysis in real time, it could be used as near fall detector 20 in the example of FIG. 1.

In this embodiment, a local processor 35 may be included in housing 30, for example, primarily to manage operation of the portable device 20. Local processor 35 may accordingly be relatively less powerful than remote processor 34 (e.g. lower requires less power). In some embodiments local processor 35 may perform a portion of the data processing to ease the burden on remote processor 34 and/or reduce transmission volume e.g. to reduce power and/or required bandwidth. In this embodiment processor 34 may be stationary and placed at a fixed location within the range of transmission of mobile device 20. Additionally, memory module 36 may also be remotely located and connected to processor 34. Processor 34 in this embodiment is conveniently a general purpose computer such as a personal computer rather than an electronic component such as an ASIC or microprocessor, and memory module 36 may be the hard disk drive of computer 34.

The distance at which mobile device 20 may travel from stationary remote processor 34 will vary depending on the type of wireless technology used by transceiver 40 and the power available in battery 56. In some embodiments the wireless technology may be Bluetooth, which has a range of several meters. In some embodiments cellular telephone technology may be used, which has a much larger range, potentially in the kilometers. However, as the distance increases the potential for disruption in communication that would adversely affect real time feedback increases. Accordingly, this embodiment may be particularly suitable in a closed environment in which a multiple number of persons need to be monitored, such as a nursing home or a hospital. The aspect of multiple patients each having a mobile device 20 and sharing remote processor 34 is represented in FIG. 2B by multiple dashed rectangles 20.

FIG. 2C shows another embodiment of near fall detector 20. This embodiment is similar to the embodiment of FIG. 2B in that processor 34 is remote and housing 30 includes local processor 35. However, in this embodiment there is no transceiver 40 or wireless communication between mobile device 20 and remote processor 34, and memory module 36 is connected to local processor 35 inside mobile device 20. In operation, mobile device 20 accumulates near fall data and stores the data in memory module 36 for later offline processing by remote processor 34. The data may be transferred to remote processor 34 through external interface port 44 in the manner described previously. In this embodiment user interface 38 is optional. In some embodiments there is no user interface 38 other than in some embodiments, on/off switch. In other embodiments user interface 38 may be a single element such as display screen 46, to guide the user in setting up the device. If this embodiment does not provide real time analysis and feedback, it is optionally not used as near fall detector 20 in the example of FIG. 1.

In some embodiments, detector 20 is configured to detect gait irregularity based acceleration measurement. In some embodiments, detector 20 is further configured to generate cuing signals responsive to detection of a gait irregularity. For example, using speaker 48 to sound messages such as 'step . . . step . . . ', and/or generate audible 'ticks' akin to a metronome, or any sound to indicate a regular pace. As another example, a vibrator is attached to the person arm and/or or optionally comprised in detector 20, and vibrations are generated to indicate a regular pace. In some embodiments, other methods are used to indicate or prompt a regular pace, such as sending an audible prompt to a earphone or hearing aid by a Bluetooth connection or a wire connection.

Optionally or alternatively, detector 20 is configured to assist in detecting tendency to fall in during a Timed Up and Go (TUG). For example, detecting rate of change of acceleration during sitting or rising movements and determining if the person is prone to fall according to threshold criterion of the rate of change. In some embodiments, the determined tendency to fall (and/or lack thereof) is reported on display screen 46. Optionally, rate of change and, optimally, the criterion that was used is reported on display screen 46. In some embodiments, the rates of change and criterion used are stored in detector 20 for further study. In some embodiments, the rates of change and criterion used are transferred to other devices as described above.

In some embodiments, determination of gait irregularity and/or tendency to fall is based on the measurement or an accelerometer such as sensor 32. Optionally or alternatively, additional or different accelerometers or sensors are used.

In some embodiments, configuring detector 20 is carried out by modifying the software program and/or electronic circuitry (e.g. re-programming an FPGA). Optionally, in case sensors other than senor 32 are used, the program and/or electronic circuitry are adapted to the other sensors. In some embodiments, in configuring detector 20, processor 34 may be changed and/or an additional processor is incorporated in detector 20.

Referring to detector 20 implies, without limiting, also variations thereof or similar devices that use one or more accelerometers.

3. Exemplary Operation

Figure 3A:
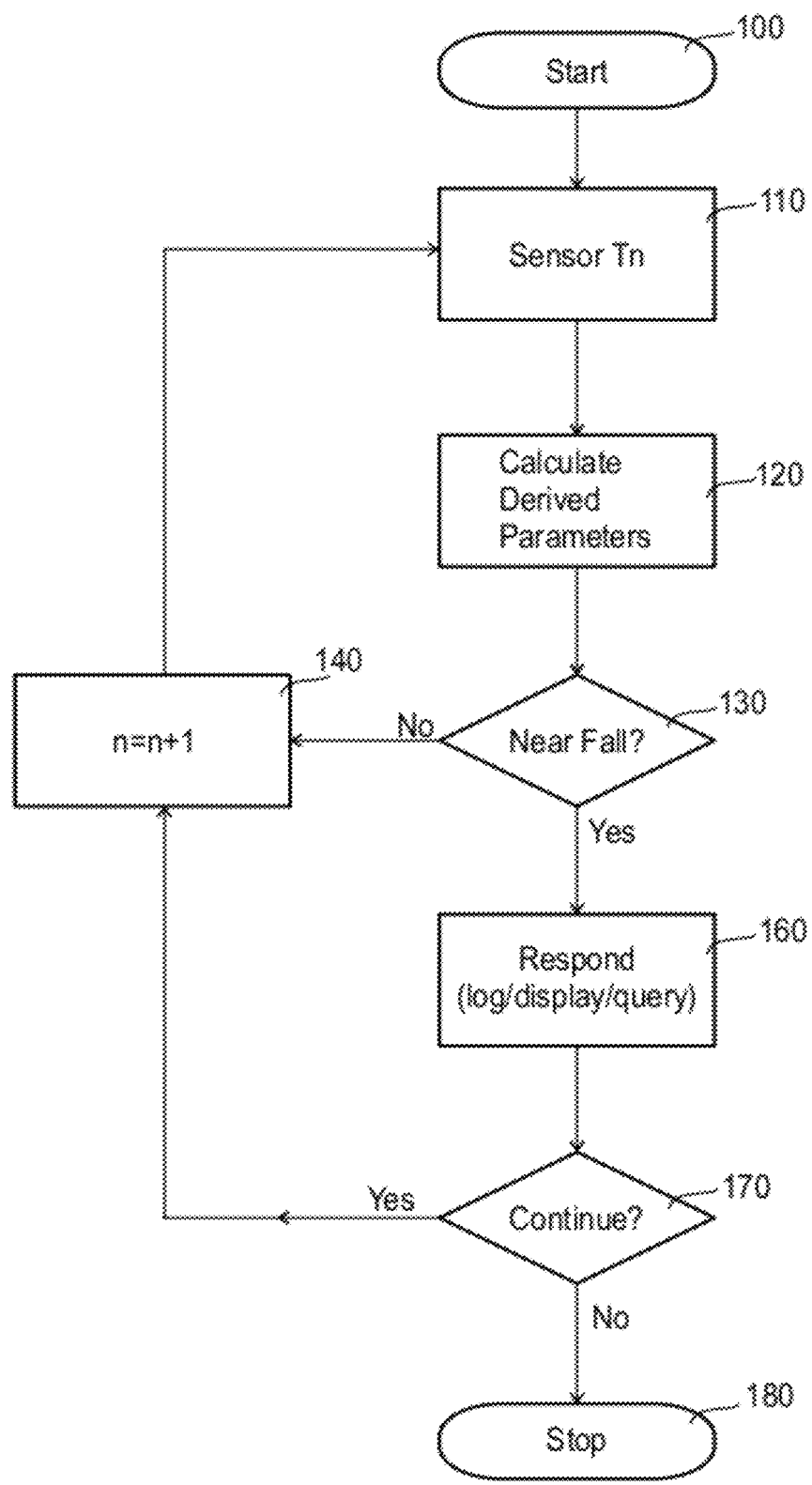
FIGS. 3A and 3B are flow charts describing a method of gait data collection, in accordance with an embodiment of the invention.
Figure 3B:
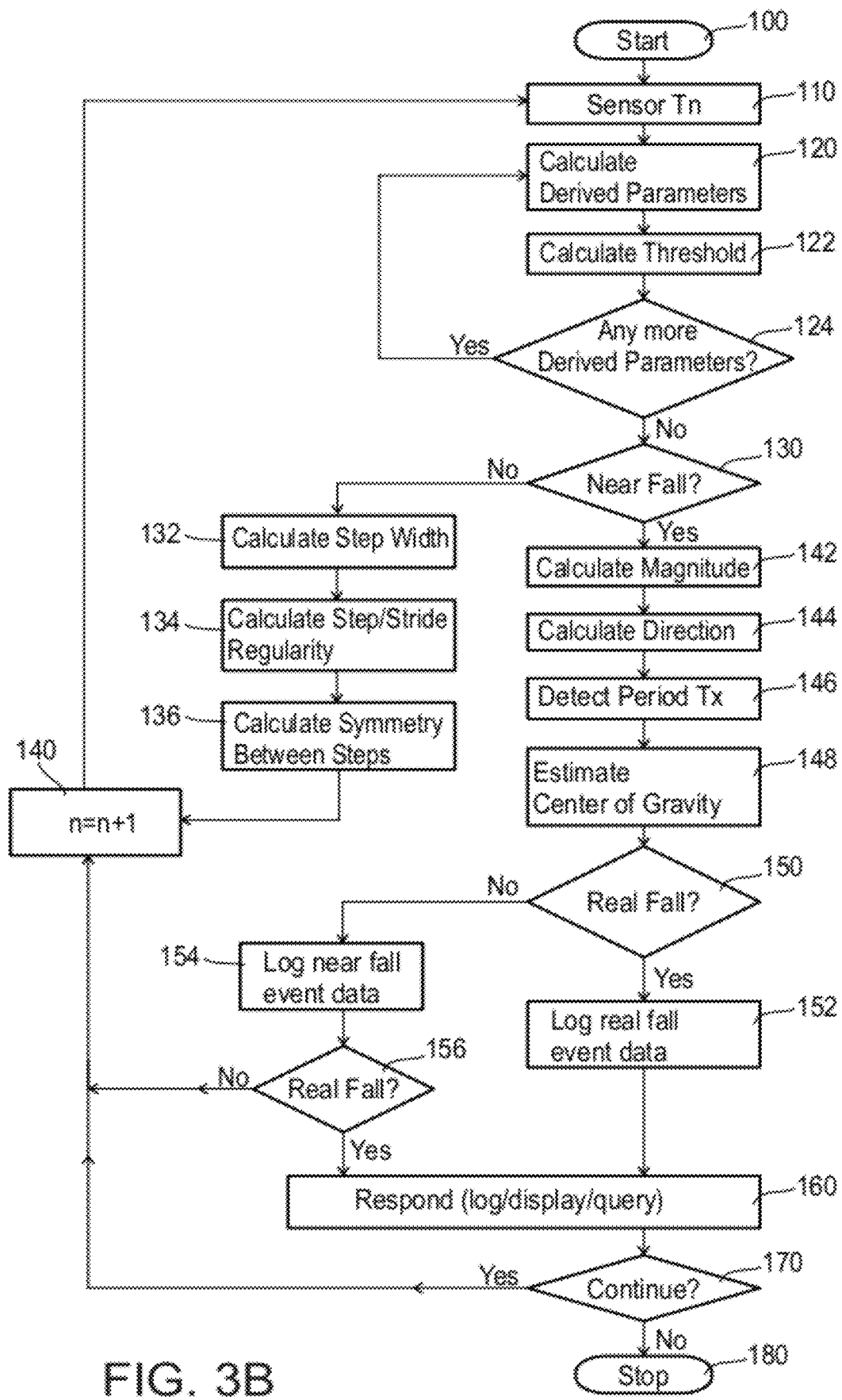

FIGS. 3A and 3B are flow charts that illustrate exemplary operation of near fall detector 20, according to an embodiment of the invention. FIG. 3A provides a broad overview and FIG. 3B provides a more detailed view of the method of gait data collection of the invention. The modules shown in the flow charts represent or correspond to processes and methods that can be carried out in software and executed by processor 34.

In these figures, the illustrated processes are based on an embodiment of near fall detector 20 that uses an accelerometer or other sensor 32 that measures acceleration directly or other movement parameters such as angular velocity or tilt. Embodiments of the invention that use sensors that measure different aspects of movement, such as velocity or position, may include extra steps that involve taking derivatives of velocity and/or position in order to obtain an estimate of acceleration and/or may measure movement parameters other than acceleration. It may be advantageous to use an acceleration based sensor 32 in some embodiments, since it is more accurate and enables processing with fewer steps and accordingly provides a faster overall processing time.

In exemplary embodiments of the invention, beginning with FIG. 3A, upon starting and calibrating the device, sensor 32 begins to measure acceleration for the current gait segment of time $T_n$ (module 110). The gait segment $T_n$ is simply the inverse of the sampling frequency, e.g. 0.01 seconds for a sampling frequency of 100 Hz. Acceleration is measured in the axes for which sensor 32 is configured, i.e. vertical, medio-lateral, and anterior-posterior for a tri-axial sensor.

In some embodiments, the raw acceleration data is then passed to processor 34 (module 120), through sensor output port 31 and processor input port 33. Processor 34 performs one or more calculations to obtain certain parameters that are used to obtain a gait acceleration profile of person 22. These parameters may be called "derived parameters" since they are derived from the raw movement data provided by sensor 32. Processor 34 optionally calculates a dynamic threshold for each derived parameter. The threshold is optionally "dynamic" because it is based on and updated from the stream of acceleration values received for each period $T_n$.

Upon calculation of these values, processor 34 optionally determines whether a near fall has occurred (module 130). In making this decision, processor 34 compares each derived parameter with an associated threshold value. The threshold value may be the dynamic threshold calculated earlier, or a predetermined "static" threshold. A near fall is indicated if a particular parameter exceeds its threshold. In addition to comparing individual derived parameters with their threshold, processor 34 may optionally also combine any two or more individual parameter results using logical operators such as OR and AND.

In some embodiments, upon completing a plurality of comparisons, processor 34 will make an overall determination of whether a near fall has occurred. If every comparison indicates a near fall (or optionally a subset such as a majority the number of comparisons indicate a near fall), then the determination of decision module 130 will be "Yes", a near fall has occurred. If none of the comparisons indicate a near fall, the determination will be "No", a near fall has not occurred. In most cases the results lie somewhere in between, with some comparisons indicating a near fall and some indicating no near fall. Processor 34, in some embodiments of the invention, may be programmed to assign a likelihood of a near fall according to a predetermined sensitivity set by the doctor in accordance with the particular medical profile and fall risk of the patient. For example, the physician may set near fall detector 20 to determine that a near fall has occurred if half or more of the comparisons indicate a near fall, and to determine no near fall otherwise.

As indicated in the flow chart of FIG. 3A, if it is determined that a near fall has not occurred the system moves on to the next time period $T_n$, for n=n+1 (module 140), and the process is repeated with a new sensor measurement (module 110). However, if it is determined in module 130 that a near fall has occurred, near fall detector 20 may then respond in some manner (module 160). As described earlier, the response could, for example, take the form of any one or combination of logging a record of the near fall event, prompting the user by display or audio, querying the user to obtain more information, and/or communicating with another party for assistance.

Decision module 170 asks whether near fall monitoring should continue. This will depend on the seriousness of the near fall. If the near fall was a relatively minor event that did not overly stress the user then control passes to module 140, "n" is incremented, and the process repeats at module 110. Otherwise near fall monitoring may stop (module 180) as the user recovers from the effects of the near fall or fall. Optionally, the stop is for a limited period of time and/or until a rest is performed.

Turning now to the flow chart of FIG. 3B, the processes performed by near fall detector 20 may now be reviewed in greater detail. Again, upon startup and calibration (module 100), sensor 32 measures acceleration for the current gait segment of time $T_n$ (module 110). In module 120, as noted, processor 34 calculates derived parameters of acceleration (and/or other movement signals).

The derived parameters in some embodiments may include, for example, any one or combination of the following six example parameter types:

1) "Max" is the maximum measured acceleration value. For example, a measurement of acceleration along the vertical ("y") axis that is the maximum such value for a period of time may be referred to as "Vertical Max".

2) "Maxp2p" is the maximum peak-to-peak value (positive peak to negative peak within a single cycle) of the measured acceleration over a period of time.

3) "SVM" is the signal vector magnitude. This is calculated as the square root of the sum of the squares of the measured acceleration, for each axis measured. For example, using a tri-axial sensor 32, SVM is the square root of the sum of $(x^2+y^2+z^2)$, where x, y, and z are the measured acceleration values in the medio-lateral ("x"), vertical ("y"), and anterior-posterior ("z") directions.

4) "SMA" is the normalized signal magnitude area. This is calculated as the sum of the absolute values of the acceleration along each measured axis, integrated over time "t". The sum is divided by "t" to obtain the normalized value.

5) "Maxdiff" is the maximum acceleration derivative. This is obtained by taking the derivative of the measured acceleration (sometimes called the "jolt"), and is the maximum of this value.

6) "Maxp2pdiff" is the maximum peak-to-peak acceleration derivative. Like Maxdiff this is also based on the acceleration derivative or jolt rather than the raw acceleration value. This parameter is the maximum value between positive peak and negative peak of the acceleration derivative within a single cycle over a period of time.

The inventors have observed that use of the above six parameters, and even a small subset of the six including as few as one or two parameters, have provided adequate results in some embodiments. In some embodiments, additional derived parameters other than the six described above may also be calculated by processor 34 and used to determine near falls, optionally in a more robust manner.

In some embodiments, the "Vertical Max" parameter is included, solely and/or in combination with other parameters, in the determination of a near fall.

Returning to the flow chart of FIG. 3B, in module 120 processor 34 calculates or updates an incremental value for a particular derived parameter. In module 122, processor 34 updates a dynamic threshold value for this parameter. In module 124 the system queries whether there are any other derived parameters to be calculated. If the answer is "Yes" control is returned to module 120 and the process repeats. Accordingly, if for example the system is programmed to use three derived parameters, then modules 120 to 124 will loop three times before proceeding to module 130. Alternatively, a flow process in which processor 34 calculates all of the derived parameters first, and then calculates all of the associated thresholds is also comprehended by the present invention. In embodiments that use a static threshold instead of a dynamic threshold, module 122 may be bypassed or its results ignored. In embodiments that use only one derived parameter, decision module 124 may be bypassed.

The calculation of dynamic threshold for each derived parameter in module 122 may be performed in a variety of ways. In some embodiments, a mean and standard deviation of the parameter may be calculated and updated with each successive measurement. The threshold may then comprise the mean value plus some multiple of the standard deviation. For example, a "usual-walk" period of time may be identified, based perhaps on measures of rhythmicity and regularity, and one or more derived parameters and their mean and standard deviations estimated based on this usual-walk episode. If in any subsequent window of time the value of one of these derived parameters exceeds the mean plus three times the standard deviation of that observed during the usual-walk, the algorithm will record this parameter as detecting a near fall. For other activities, such as stair climbing (e.g., similarly identified from the gait signals, or based on displacement as a function of time), other thresholds may be applied. Optionally, a user can indicate, for example, during a calibration stage, if a recent event was a near fall or not. This may be, for example, initiated by the user, or by the system asking regarding a specific event.

Unlike the dynamic threshold, the calculation of the static threshold is optionally performed offline, at some time prior to operation of the near fall detector 20. Parameter data may be obtained for a time period in which a person's walk is directly observed (or recorded for later observation). From this, two groups of time periods or intervals may be defined, comprising "near fall" groups and "non-near fall" groups. Since the near fall groups have been directly observed and are known to be accurate, they comprise a "gold standard" of known near falls that may be correlated with the signal processing data.

In some embodiments, the static threshold may be calculated as an optimization of sensitivity and specificity with respect to a single or multiple number of derived parameters. The algorithms used may be non-linear and advanced. Some examples of the types of discriminant functions that may be employed include linear, diaglinear, quadratic, diagquadratic, and mahalanobis. Algorithm performance may then be measured in terms of sensitivity (true positive/(true positive+false negative)) and specificity (true negative/(true negative+false positive)).

In decision module 130 processor 34 determines whether a near fall has occurred in time period "n" based on the updated derived parameter values. As noted above, the determination may be made by subtracting (or comparing in another way) from the derived parameter value the value of its associated threshold. In embodiments that use dynamic thresholds, the threshold values calculated in module 122 are used. In embodiments that use static thresholds, the threshold values will have been pre-loaded in memory and may be retrieved at the time of the calculation. Also as noted, in some embodiments a plurality of such comparisons are made involving individual parameters and combinations of parameters.

The inventors have discovered that, in some embodiments, adequate detection of near falls may be obtained through the calculation of a single derived parameter, Maxp2pdiff, based on acceleration along the vertical axis. The inventors observed that vertical Maxp2pdiff identified near falls with a sensitivity of 85.7% and a specificity of 88.0%. It may be noted that in this case, decision module 130 would only need to review a single comparison of Maxp2pdiff with its associated threshold, as no other comparisons need to be considered.

The inventors have also discovered that, in some embodiments, adequate detection of near falls may be obtained through the calculation of two derived parameters, Maxp2pdiff and Max, both based on acceleration along the vertical axis, and by performing a logical AND operation on the individual results. Accordingly, this method will find a near fall only in the event that both parameters exceed their respective thresholds. The inventors observed that this method of detection identified near falls with a sensitivity of 85.7% and a specificity of 90.1%.

Figure 4:
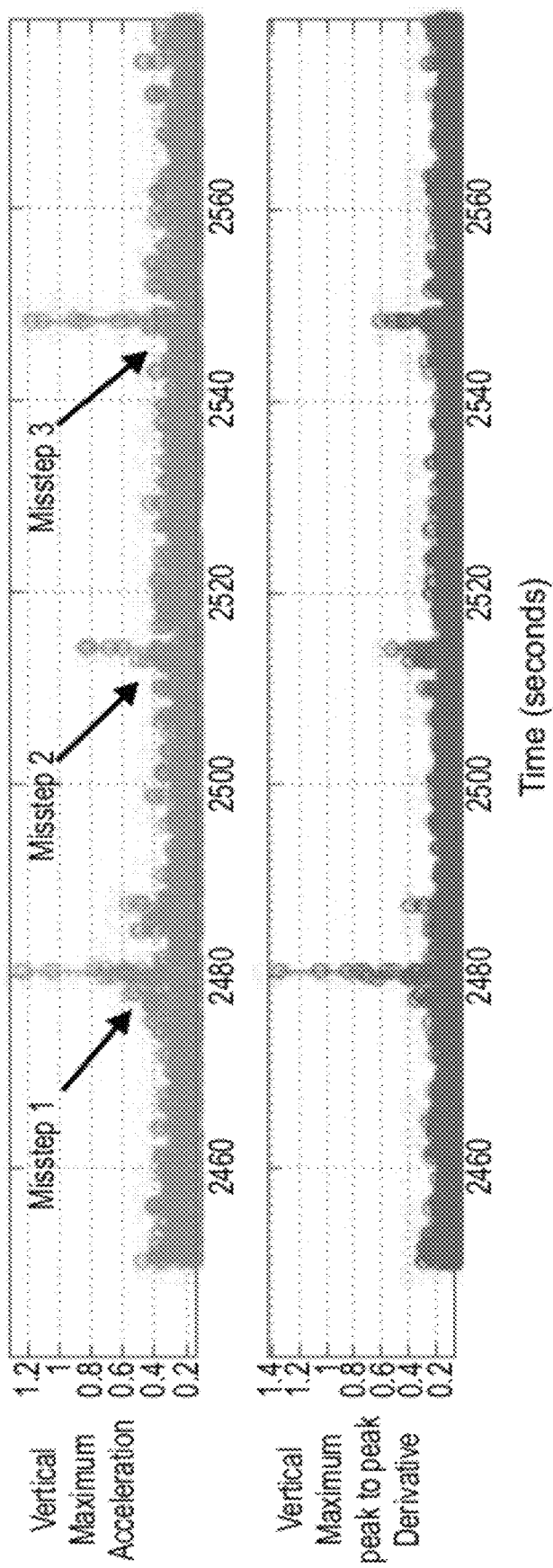
FIG. 4 shows graphs of derived parameters Vertical Maximum Acceleration and Vertical Maximum Peak to Peak Derivative, in accordance with an embodiment of the invention.

An illustration of the results using the above methods of detection is shown in FIG. 4. As indicated, in the time period recorded in the graphs, person 22 had three near falls or missteps. In FIG. 4, the lower graph shows Maxp2pdiff and the upper graph shows Vertical Max over this time period. It may be seen that at or about the time of each misstep, both derived parameters display distinct increases in value relative to their average values over the balance of the time period. Accordingly, a gait acceleration profile based on the derived parameter Maxp2pdiff, or one based on the logical combination of Maxp2pdiff "AND" Vertical Max, may be used to detect near falls with adequate results.

As noted, the present invention comprehends many other selections of specific derived parameters and combinations of derived parameters to determine near falls. In another example, all six derived parameter examples may be calculated, and near falls could be determined if any three or more confirm a near fall. Through logical combinations of individual parameters many more comparisons may be made and considered in determining a near fall to enhance robustness of the decision tree. The various comparisons could be listed in a hierarchy and determination of a near fall could be made along a gradient that corresponds with the results of the plurality of comparisons. The output could be binary (i.e. "yes/no" a near fall has likely occurred) and/or a continuous measure related to the likelihood that a near fall has occurred, based on the number of parameters exceeding thresholds. For example, an embodiment may have 100 comparisons involving the different parameters individually and in various logical combinations. The comparisons could represent 100 "levels" over which the near fall is graded, ranging from a sure near fall at one end to a sure non-near fall at the other end. Similarly, output scores could be graded based on the percent of steps in which a misstep occurred.

Optionally (e.g., as discussed above), the determination of a person's near fall experience may be used to prepare or modify that person's gait acceleration profile. Near fall detector 20 may also be used in some embodiments to determine other aspects of a person's gait that enhance the gait acceleration profile. For example, if a near fall has occurred, it is useful to know the magnitude and direction of the near fall. It is also useful to know (e.g. detect or note) if the incident has resulted in an actual fall. Other useful gait parameters arise from a study of the person's walking motion, and include, for example one or more of, step width, step or stride regularity, and symmetry between steps.

The calculation of gait parameters that arise from the near fall may be seen in flow chart of FIG. 3B in the series of modules that follow a "Yes" determination of module 130.

In module 142, the magnitude of the near fall is optionally determined. Magnitude may be obtained from the peak of the acceleration, i.e. the derived parameter Max. Alternatively, in some embodiments that calculate the derived parameters SVM and/or SMA, these parameters may be used individually or in combination to obtain a better quality of the magnitude of the near fall. A magnitude value derived from SVM and/or SMA is considered to be more robust and stronger than a value derived from acceleration data alone. The magnitude value may be converted and presented on a number on a scale, for example between 1 and 100. In reviewing a person's gait acceleration profile, it is helpful to know that the person's near falls had an average magnitude of 70, for example, as opposed to an average magnitude of 20.

In module 144, the direction of the near fall is optionally determined. This parameter can enhance the ability to extract meaning, at least as an estimation, and interpret the gait acceleration profile by providing the direction of a near fall relative to vectors along the vertical, medio-lateral, and anterior-posterior axes. It may be noted that in order to obtain directional near fall information sensor 32 is optionally configured to obtain measurements along all three axes.

The directional information provided by this parameter may be useful in aiding diagnosis by a physician. For example, falls that occur to the side are more likely to result in a broken hip, which are particularly troublesome and dangerous to elderly persons. Accordingly, the awareness of such data may trigger preventive action that could prevent a disabling fall that might otherwise occur. In another example, a persistent trend to near falls in a particular direction might indicate a structural weakness or postural problem, which may lead to preventive physiotherapy, adoption of a walking aid, or wearing asymmetrical protection such as a pad on one hip.

Optional modules 146 and 148 optionally provide information that assists in determining if a real fall has occurred. After a real fall, there is often a silent period since the person is not moving. Accordingly, module 146 collects sensor information for a period $T_x$ after the near fall. If the measured values are zero or close to zero (or reflect a vertical location that is near the floor and/or a small range of motion (e.g., by integrating acceleration over time)), it would suggest that a real fall has occurred. Module 148 estimates the height or position of the person's center of mass after the near fall. The center of mass may be estimated from a gyroscope, if that instrument is provided in near fall detector 20. In some embodiments, an accelerometer such as that used for sensor 32 may be used to estimate the height of the center of mass.

Decision module 150 optionally considers the above information in determining whether a real fall has occurred. This module may also consider the magnitude value obtained in module 142, since in a real fall the magnitude value tends to be higher than for a near fall. If a real fall is determined, module 152 logs data relating to the incident, such as the time and day, magnitude, and direction. In module 160, near fall detector responds in the manner described earlier, by interacting with the person and possibly contacting an outside party. If module 150 determines that a real fall has not occurred, the event is logged as a near fall (module 154). An optional module 156 may consider the parameters of the near fall in deciding whether to respond (module 160), or whether to proceed to module 140 to increment "n" and repeat the sequence at module 110.

Returning to decision module 130, if processor 34 determines that a near fall has not occurred, gait parameters such as step width, step or stride regularity, and symmetry between steps may optionally be determined. These parameters can provide additional information about the patient's balance and gait that can not be obtained simply by observational analysis or self-report. These parameters are also independent of one another, and accordingly provide complementary, objective data that enhances the quality of the patient's gait acceleration profile.

Beginning with optional module 132, the step width parameter may be determined as the distance in the horizontal or medio-lateral direction between the subject's feet, orthogonal to the direction of movement. It may be noted that to calculate step width sensor 32 is optionally configured to measure along the medio-lateral axis. It may also be noted that step width is a distance value. Accordingly, if sensor 32 is an accelerometer that measures acceleration directly, the measured value would generally have to be further processed, such as by double integration, to obtain an estimate of the step width distance.

The step width parameter may be useful for the gait acceleration profile of a patient in that if it is found to be wide, it may be an indication that the patient is over compensating. A step width that is not consistent and is too variable is considered to be unhealthy, and accordingly may prompt further diagnostic testing by the doctor.

Optional module 134 may be used to calculate step or stride regularity. This parameter is a measure of the repeatability, regularity, or consistency of the person's gait, and can refer to the length or the timing of the step. Useful information may be obtained along a single axis or from all three axes. This parameter is typically calculated by an autocorrelation of the raw acceleration data.

A stride of walking is the time to complete one walking cycle, for example from the left foot touching the ground to the subsequent instance of the left foot touching the ground.

One stride equals two steps. Accordingly the terms "step regularity" and "stride regularity" mean essentially the same thing, with the only difference being the portion of the gait cycle over which they are measured.

Measures of regularity can be used to define the degree to which the person's walking pattern is rhythmic. In medical terms, the greater the regularity and "rhythmicity", the healthier the motor control system is considered to be in the patient.

Optional module 136 may be used to calculate symmetry between steps. This parameter measures the degree of equality between steps taken by the left foot relative to steps taken with the right foot. It may be calculated by the formula:

Gait Asymmetry=100×|ln(SSWT/LSWT)|.

In the formula, "SSWT" and "LSWT" stand for the mean values of the Short and Long Swing Time, respectively, as determined from the vertical axis.

Other measures of asymmetry, such as one based on step times, for example, may also be used in some embodiments to provide a more complete estimate of asymmetry patterns.

For example, identifying cycles periods in accelerometer signal or signals (e.g. peak to peak) and determining the variability (the irregularity) of the cycles' periods.

In some embodiments, an asymmetry measure such as difference between the longest and shortest cycles may be used. Optionally or alternatively, the standard deviation of the cycles' periods may be used. Optionally or alternatively, some other statistics such as the median of the period may be used.

In some embodiments, a measure of regularity of asymmetry may be obtained in a frequency domain, optionally within locomotion band (stride) such as 0.5-3.0 Hz. A narrow frequency spread (e.g. standard deviation) indicates regular stride and, vice versa, wide spread indicates irregularity and possibly a sign of physiological or neurological disorder.

Figure 5:
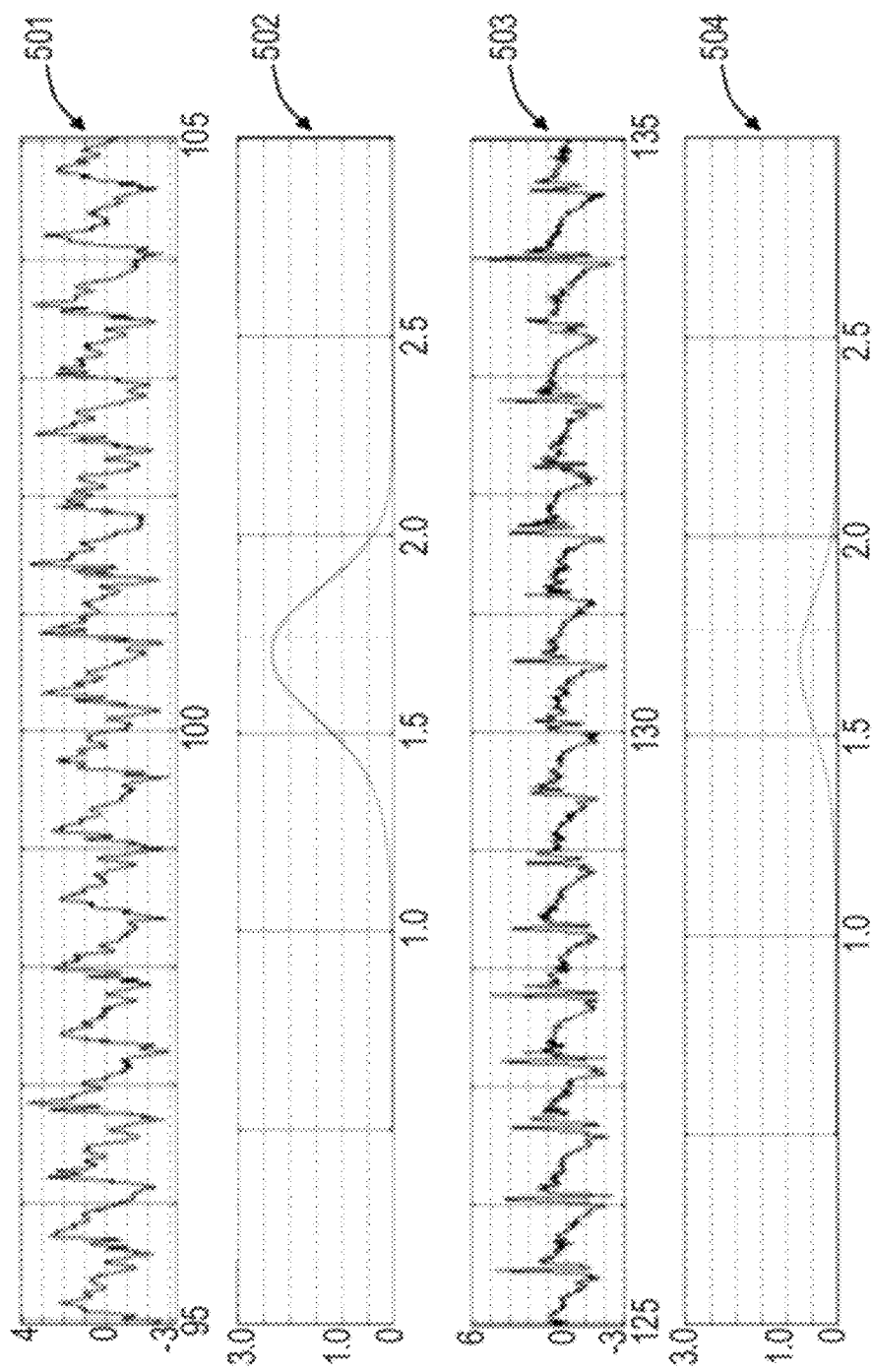
FIG. 5 shows exemplary charts of stride acceleration and frequency spread of a healthy person and a person with Parkinson disease, respectively.

FIG. 5 shows exemplary charts of stride acceleration and frequency spread of a healthy person and a person with Parkinson disease, respectively.

Charts 501 and 503 are of a healthy and Parkinson diseased persons, respectively, illustrating the acceleration in the anterior-posterior direction, and charts 502 and 504 illustrate the respective frequency range. Vertical axis of charts 501 and 503 is acceleration (in g) and the horizontal axis is in seconds; horizontal axis of charts 502 and 504 is in Hertz and the vertical axis is the frequency amplitude.

The sharper and narrower peak of chart 502 with respect to chart 504 reflects a more consistent gait pattern, i.e., reduced gait variability and lower stride-to-stride fluctuations of a healthy person relative to a Parkinson diseased person.

In some embodiments, a measure of stride regularity or asymmetry is determined by combining (e.g. averaging) two or more of the methods described above. Optionally, the combination assigns different weights to the various measures obtained by the methods described above. In some embodiments, measures that indicate larger asymmetry are assigned larger weights relative to measures that indicate smaller asymmetry.

Upon completion of the calculation of the various gait parameters, module 140 increments "n" and the process is repeated with a new sensor measurement for time period $T_n$ in module 110.

A further aspect of operation of some embodiments of near fall detector 20 concerns calibration of the device. Calibration initializes the device so that the sensor recognizes and accurately responds to movement along the appropriate axes. In this way, near falls and other gait parameters can more accurately be measured. Calibration is helped by measuring along all three axes, as this enables the device to find the direction of gravity and to orient itself to align with it.

In an exemplary embodiment of the invention, calibration involves performing procedures recommended or instructed by the sensor or accelerometer manufacturer. In some embodiments of the invention, such as for example where near fall detector 20 is a dedicated device worn on the person's belt, the orientation of the device in space is relatively fixed. Accordingly, calibration in these cases may be a relatively simple matter. In other embodiments of the invention, such as when near fall detector 20 is incorporated in another device such as a cell phone, the orientation of the device in space is not fixed and will vary widely in the course of daily use. For example, a cell phone may be vertical when in use by a standing person, but may be horizontal if the person is lying down. Further, when put in a coat pocket or carrying bag the cell phone may be upside down or adopt any other orientation at random. In these cases the device may self-calibrate to ensure that near fall detector 20 works properly.

In some embodiments of the invention, calibration and operation of the device may be independent of the weight of the person whose movement is being monitored. For example, near fall detector 20 will be calibrated and operate in the same manner whether the user is a heavier person or a lighter person.

4. Exemplary Applications of Gait Acceleration Profile

As discussed, the gait acceleration profile of a person comprises that person's observed or recorded gait parameters over one or more periods of time. For example, a sample gait acceleration profile of a particular person might be: patient experienced three near falls over a two day period. The near falls had magnitudes of 60, 23, and 47 (arbitrary units) and were primarily in the medio-lateral/left direction. During this period, step width was 0.31 meters, stride variability (inversely related to regularity) was 6%, and gait asymmetry was 17. After an intervention consisting of physiotherapy and prescribed medication, in an evaluation over a similar two day period, near falls dropped to one with a magnitude of 14. Step width narrowed to 0.26 meters and gait asymmetry also improved by a reduction to a value of 11.

Some embodiments of the invention may enable the benefits of a detailed patient gait acceleration profile to become available at greater convenience to both doctors and their patients. An example of this may be in the area of remote exercise monitoring. There is a growing push in the medical field for at-home interventions to improve mobility. A doctor may encourage an older adult or patient with Parkinson's disease to walk for thirty minutes, five times a week, with three sessions outside and two sessions indoors on a treadmill, the latter perhaps having more complex instructions. Near fall detector 20 in some embodiments may be used for real-time monitoring as the patient carries out the prescribed exercises. If a near fall occurs, an alarm can sound or assistance provided immediately. In this way the safety and usability of such "tele-rehabilitation" approaches are improved, while at the same time enabling patient progress to be closely and precisely monitored. Alternatively, the near fall detector can be used to assess the efficacy of the prescribed therapy.

In some embodiments, detector 20, or a variation thereof, may be used or adapted (e.g. by software and/or circuitry modification) to enhance common screening of subject prone to falls or to near-falls, as described below.

The Timed Up and Go (TUG) test is a widely used clinical test of fall risk. Subjects are asked to start in a seated position, stand up and walk 3 meters, turn around, and return to the seated position. In older adults and other populations such as patients with Parkinson's disease (PD) or stroke, longer TUG times have been associated with impaired mobility and an increased fall risk (for example, Balash Y, Peretz C, Leibovich G et al. Falls in outpatients with Parkinson's disease: frequency, impact and identifying factors. *J Neurol* 2005; 252:1310-1315; Najafi B, Aminian K, Loew F et al. Measurement of stand-sit and sit-stand transitions using a miniature gyroscope and its application in fall risk evaluation in the elderly. *IEEE Trans Biomed Eng* 2002; 49:843-851; Podsiadlo D, Richardson S. The timed "Up & Go": a test of basic functional mobility for frail elderly persons. *J Am Geriatr Soc* 1991; 39:142-148).

However, the TUG does not always successfully identify those with a high fall risk, especially among relatively well-functioning, healthy older adults (for example, Buatois S, Gueguen R, Gauchard G C et al. Posturography and risk of recurrent falls in healthy non-institutionalized persons aged over 65. *Gerontology* 2006; 52:345-352; Marschollek M, Nemitz G, Gietzelt M et al. Predicting in-patient falls in a geriatric clinic: a clinical study combining assessment data and simple sensory gait measurements. *Z Gerontol Geriatr* 2009; 42:317-321).

It was observed by the inventors, at least in representative cases, that extracted accelerometer-based measures such as by device 20 or similar ones can distinguish or be adapted to distinguish (e.g. by software adaptation) between elderly fallers and elderly non-fallers when they perform the TUG, even if TUG duration times are not significantly different in the two groups. It was observed that the rate of change of the acceleration during sitting movement from standing position and during movement of rising from a seated position is different between healthy persons and fallers (persons prone to fall, having a tendency to fall). Healthy persons exhibit a significantly larger rate of change of the acceleration relative to fallers, at least as observed for elderly subjects.

Figure 6:
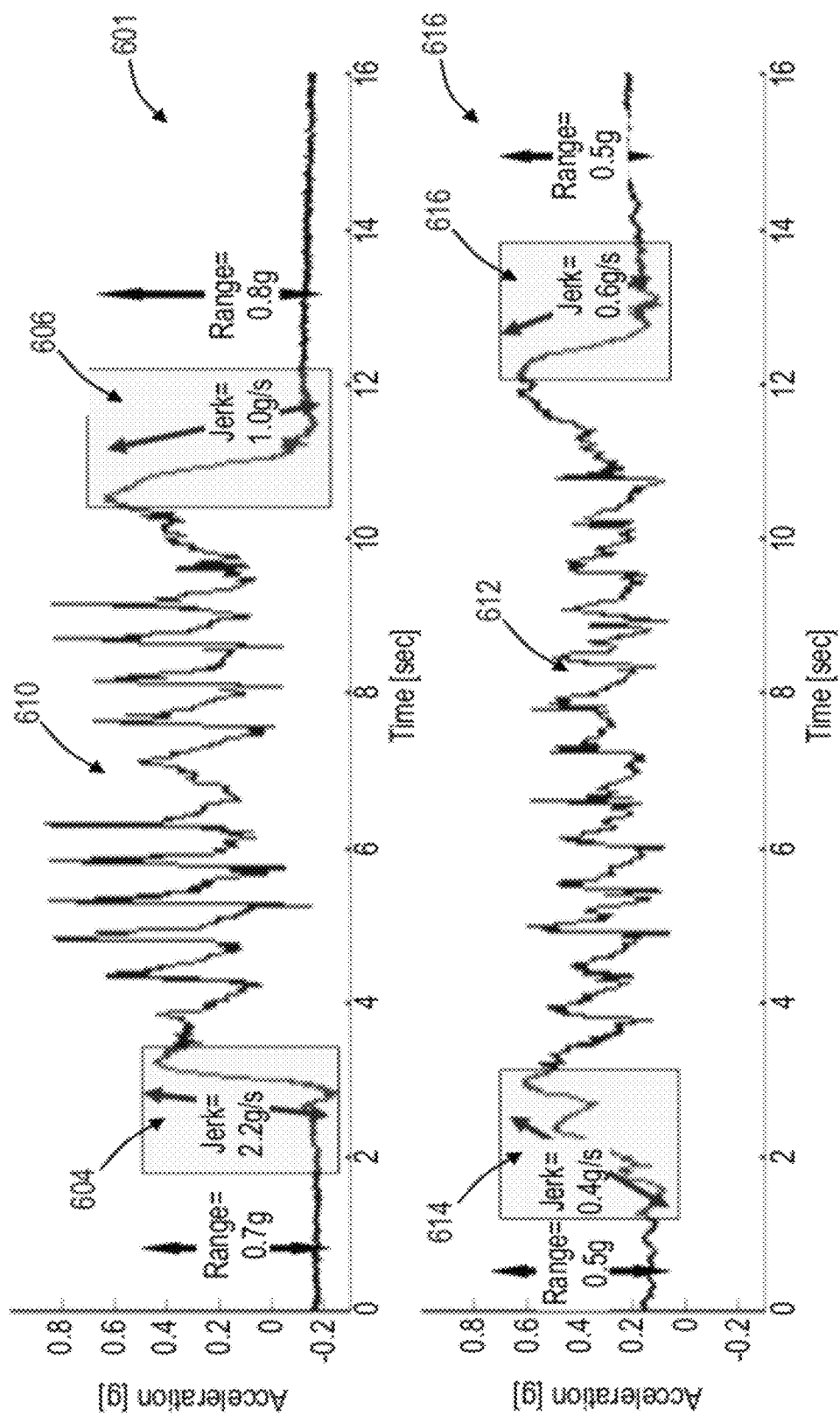
FIG. 6 shows exemplary charts of Timed Up and Go (TUG) of healthy person and a person prone to falling, respectively.

FIG. 6 shows exemplary chart 601 of Timed Up and Go (TUG) of healthy person and 602 of a person prone to falling ('faller'). Charts 601 and 602 illustrate anterior-posterior accelerations measured with an accelerometer, where the horizontal axis is in seconds and the vertical axis is in –g. The acceleration signals of charts 601 and 602 are generally divided, respectively, into three zones, namely, 604 and 614 are when the persons sit from a standing position, 610 and 612 are walking periods, and 606 and 616 are when the persons stand from a seated position.

In the regions of up or down movements 604, 606, 614 and 616 the rate of change of the acceleration was determined as a time derivative of the measured accelerations (in g/sec), indicated in FIG. 6 as 'jerk'.

As illustrated in FIG. 6, the rate of change of acceleration of the jerks of the healthy person and the faller person are considerably different. The rate of the acceleration of the healthy person is higher than that of the faller person. For example, as illustrated, the upward jerk of the healthy person is about 2 g/sec and the downward jerk (at 606) is about 1 g/sec, wherein the respective jerks of the faller are about 0.5 g/sec, (at 614 and 616, respectively).

As detector 20 comprises accelerator and measures acceleration and rate of change of acceleration, in some embodiments detector 20 is modified or adapted to distinguish (screen) fallers from non-fallers based on the amount of the rate of change of the acceleration in the jerks zones. Thus, in some embodiments, detector 20 can augment the TUG test by providing indication for differentiation between healthy persons and persons prone to fall, at least in some cases.

In some embodiments, modifying of adapting detector 20 comprises modifying the software program and/or circuitry of the detector (e.g. different gate array layout). In some embodiments, the modified or adapted detector 20 provides control (e.g. by touchscreen or button) to indicate when to measure the jerks. Optionally or alternatively, the program is adapted to recognize jerk zones according relative long generally monotonic acceleration with respect to walking.

In some embodiments, detector 20 is capable to determine gait irregularity and asymmetry, as described above. As such, further to a diagnostic tool, in some embodiments detector 20 can be used as a therapeutic or an assisting device for regulating the gait of a subject having a neurological disease or another subject having a tendency to fall.

For example, with ongoing assessment of the pattern and regularity of a gait of a subject, a signal could be automatically generated responsive detection of deviation from sufficiently regular or expected gait pattern.

In some embodiments, the signal indicates that the gait is irregular or that the subject is about to fall (near fall), prompting the subject to recover a proper gait. Optionally or additionally, the signal indicates suggested gait pace that the subject can follow in order to stabilize the gait (cueing signals).

In some embodiments, the signal indicates suggested pace irrespective of irregularities, providing continuous training to the subject, at least for certain time periods. Optionally the training may, in some cases at least, enhance functional mobility of the subject.

In some embodiments, upon detection of a near fall situation or irregular pace, detector 20 generates an alarm message such as by speaker 48, notifying the subject of the situation.

In some embodiments, upon detection of irregular pace, detector 20 generates audible messages guiding the subject pace, such as 'step . . . step . . . ', thereby assisting the subject to regulate and stabilize the gait. In some embodiments, the guided pace is within a determined variability, avoiding too 'mechanical' gait. In some embodiments, the guided pace is adapted and/or synchronized with the subject's pace.

In some embodiments, the pace of the cueing signals are based on behavior detected or assessed in healthy persons, optionally of about the same age. Optionally or additionally, the pace of the cuing signals are based on intervals where the subject's gait is determined to be regular, at least to some extent.

In some embodiments, one or more other signals are generated in addition or instead the audible messages described above. For example, rhythmic auditory stimulation by tone such as or similar to a metronome, or rhythmic visual stimulation by one or more of alarm lights 50 or indications on display 46.

In some embodiments, detector 20 is augmented to comprise a vibrator (e.g. akin to some pagers or cellular phones) and vibrations are generated to indicate the gait situation or provide pace guiding signals.

The amount of gait acceleration information that may be made available for analysis may be greatly increased due to the convenience provided by near fall detector 20 in this application. This in turn may lead to improvements in patient cognitive and motor functioning, particularly since available data suggest that interventions are more effective when they take place over longer time periods, are individually tailored, and include exercise in the home environment.

Near fall detector 20, in some embodiments of the invention, may even be incorporated into treadmills or other exercise equipment, or provided as an add-on accessory. The device could be in the form of a "smart-box" that contains the software, processor 34, communication hardware, and other elements. When using this type of exercise equipment, the user could indicate that he or she is doing a special activity for monitoring for near falls. In some embodiments the device may adjust the parameter threshold values to account for planned variations in exercise stimulation, such as increases in treadmill speed designed to challenge the patient.

The information provided by the gait acceleration profile may also provide insight into a person's neurological state related to the diagnosis of other types of medical conditions besides the predilection to fall.

It is hypothesized that a gait profile based on acceleration and other measures of movement (e.g., gyroscopes, tilt sensors) that includes such information as near falls, step and stride regularity, and symmetry may be tracked as part of a patient's medical record, and used as a tool for therapeutic use.

For example, in many cases prior to falling, there is an instant or moment in time when the person's brain fails to operate properly. In most cases this aspect of the person's medical condition may not be detectable until the symptoms become more pronounced and the underlying disease becomes more severe. However, in some cases the reduced brain activity may be observable indirectly, through the person's motor output or gait. By monitoring gait with near fall detector 20 of the present invention, the person's quality of movement may provide an early warning indicator of the onset of Parkinson's disease, for example, or other movement disorders.

In another example, a physician may have an array of possible treatments available for a patient diagnosed with a particular illness. One of the possible treatments may be a drug that is known to be effective with some patients but not with others, but for which there is no methodology to discern beforehand whether a particular patient will benefit. Upon further research using the gait profile, it may be found that the gait profile provides the missing neurological information to assist the physician in determining whether the drug will be effective in that case. Used in this way, the gait profile may lead to better and more cost effective medical care. Further, the efficacy of treatment may be verified by continuing to monitor the gait profile, and by analyzing subsequent near fall data to confirm that the number of instances of near falls and/or their magnitude has declined.

As used herein the term "about" refers to ±10%.

The terms "comprises", "comprising", "includes", "including", "having" and their conjugates mean "including but not limited to".

As used herein, the singular form "a", "an" and "the" include plural references unless the context clearly dictates otherwise.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A method of determining gait irregularity, including near fall events, in an event of which a user recovers from a momentary loss of balance during the gait, the method comprising:
   electronically collecting movement data using a single detector configured to measure acceleration of the user's body, said detector configured to be located at a single location on the user's body, wherein said collected movement data is collected by said single detector, wherein said single location is a torso of the body;
   using a processor in communication with said detector, electronically determining a movement parameter value from said data collected at the single location on the user's body, wherein said movement parameter value comprises a measure of maximum acceleration, and wherein said movement parameter value relates to a movement parameter in a substantially vertical direction;
   electronically comparing, using said processor, said movement parameter value determined from said data collected using said detector with a threshold value, wherein said electronically comparing comprises comparing said measure of maximum acceleration with said threshold value to identify near fall events during the gait;
identifying near fall events during the gait using a result of said comparing; and
electronically storing a count of a plurality of near fall events in a memory.

2. A method according to claim 1, wherein the method comprises determining a fall.

3. A method according to claim 1, wherein determining comprises matching a pattern with respect to time of the movement data with a reference pattern.

4. A method according to claim 3, wherein the reference pattern represents proper gait pattern.

5. A method according to claim 3, wherein the reference pattern represents improper gait pattern.

6. A method according to claim 3, wherein the reference pattern represents a gait pattern exhibiting at least one near fall event.

7. A method according to claim 3, wherein the matching classifies the data as exhibiting a fall, a near fall event, or lack thereof.

8. A method according to claim 3, wherein the matching comprises at least one of correlation, cross-correlation, wavelets matching or neural networks or a combination thereof.

9. A method of gait data collection according to claim 1, wherein said electronically comparing comprises comparing said measure of movement in the vertical direction with said threshold value to identify near fall events during the gait.

10. A method of gait data collection according to claim 1, wherein
determining from said data further includes determining a second movement parameter value,
comparing said movement parameter value further includes comparing said second movement parameter value with a second threshold value, and
counting a plurality of near fall events comprises counting at least a near fall event if said movement parameter value exceeds said threshold value and said second movement parameter value exceeds said second threshold value.

11. A method of gait data collection according to claim 10, wherein said second movement parameter value includes one of the group consisting of; a rate of change of acceleration, an angular velocity, an anterior-posterior acceleration, a medio-lateral acceleration.

12. A method of gait data collection according to claim 10, wherein said second movement parameter value relates to a movement parameter in a substantially vertical direction.

13. A method of gait data collection according to claim 1, wherein said threshold value is a predetermined value.

14. A method of gait data collection according to claim 1, wherein said threshold value is a continuously updated function of said movement parameter value.

15. A method of gait data collection according to claim 14, wherein said function is a mean of multiple movement parameter values plus a multiple of a standard deviation of said multiple movement parameter values.

16. A method of gait data collection according to claim 1, wherein said counting of near fall events provides a quantitative measure of effectiveness of therapeutic interventions.

17. A method of determining gait irregularity according to claim 1,
wherein said movement data includes cyclic acceleration data; and
electronically determining comprises:
determining from said acceleration data periods of cycles; and
identifying a gait irregularity when a period of a cycle exceeds a threshold.

18. A method of determining gait irregularity according to claim 17,
wherein said cyclic acceleration data includes peaks; and
electronically determining comprises:
determining from said acceleration data periods between said peaks; and
identifying a gait irregularity when a period between said peaks exceeds a threshold.

19. A method of gait data collection, according to claim 1, wherein said movement data includes cyclic acceleration data, each cycle including a cycle shape; and
electronically determining comprises:
determining from said acceleration data periods between said peaks; and
identifying a gait irregularity when a cycle shape varies above a threshold.

20. A method of gait data collection, according to claim 1, wherein said movement data includes cyclic acceleration data, each cycle including a cycle shape; and
electronically determining comprises:
determining from said acceleration cross-correlation between cycles; and
identifying a gait irregularity when a cross-correlation between cycles exceeds a threshold.

21. A method of gait data collection according to claim 1, wherein
electronically determining comprises:
determining from said data an acceleration frequency spread; and
identifying an irregularity of the gait from said acceleration frequency spread.

22. A method of gait data collection, according to claim 21, wherein determining said acceleration frequency spread is by using a Fourier transform.

23. A method of gait data collection, according to claim 1, comprising:
electronically determining from said movement data a step width.

24. A method of gait data collection, according to claim 1, the method comprising:
electronically determining from said movement data a step length.

25. A method of gait data collection according to claim 1, wherein said movement parameter value relates to movement in substantially an anterior-posterior direction.

26. A method according to claim 1, wherein said electronically collecting is using a sensor.

27. A method according to claim 1, wherein said counting of near fall events provides quantifiable parameters for assessing a person.

28. A method according to claim 1, wherein said identifying near fall events during the gait includes using the result of said comparing, if said determined movement parameter value exceeds said threshold value.

29. A method according to claim 1, wherein said using the processor includes electronically determining the movement parameter value from collected acceleration data alone.

30. A method of determining gait irregularity, including near fall events, in an event of which a user recovers from a momentary loss of balance during the gait, the method comprising:

electronically collecting movement data using a single detector configured to measure acceleration of the user's body, said detector configured to be located at a single location on the user's body, wherein said collected movement data is collected by said single detector, wherein said single location is a torso of the body, using a processor in communication with said detector, electronically determining a plurality of movement parameter values from said data collected at the single location on the user's body, wherein said plurality of movement parameter values comprise a measure of maximum acceleration, and where said plurality of movement parameter values includes at least one movement parameter value related to a movement parameter in a substantially vertical direction, electronically determining, using said processor, from said data at least one irregularity of the gait, including identifying near fall events during the gait, said electronically determining including electronically comparing each of said plurality of movement parameter values with an associated threshold value, wherein said electronically comparing comprises comparing said measure of maximum acceleration with said threshold value to identify near fall events during the gait, including comparing said at least one movement parameter value related to the movement parameter in the substantially vertical direction determined from said data collected using said detector with a threshold value, to indicate a near fall event when each said movement parameter value related to the movement parameter in the substantially vertical direction exceeds an associated threshold value, and electronically storing a count of a near fall event in a memory, if a predetermined combination of comparisons indicate a near fall event.

31. A method of gait data collection according to claim 30, the method comprising:

electronically recording a magnitude of said near fall event.

32. A method of gait data collection according to claim 30, wherein said predetermined combination of movement parameters is a majority of said plurality of movement parameters; and electronically counting comprises electronically counting at least a near fall event if said majority of said plurality of comparisons indicates a near fall event.

33. A method of determining gait irregularity, including near fall events, in an event of which a user recovers from a momentary loss of balance, the method comprising:

electronically collecting movement data using a single detector configured to measure acceleration of the user's body, said movement data including a measure of maximum acceleration, said detector configured to be located at a single location on the user's body, wherein said collected movement data is collected by said single detector, wherein said single location is a torso of the body, using a processor in communication with said detector, electronically extracting an indicator indicating a loss of control from said data collected at the single location on the user's body, wherein said indicator indicating the loss of control includes at least one movement parameter value which exceeds a threshold value, wherein said electronically extracting an indicator comprises comparing said measure of maximum acceleration with said threshold value to identify near fall events during the gait, wherein said movement parameter value relates to a movement parameter in a substantially vertical direction, electronically storing a count of at least a near fall event, in a memory, if said indicator indicates said loss of control, and electronically recording a date or time for said near fall event, in said memory.

34. A method of gait data collection according to claim 33, wherein said counting of at least a near fall event provides a quantitative measure of effectiveness of therapeutic interventions.

35. A method according to claim 33, wherein said counting of at least a near fall event provides quantifiable parameters for assessing a person.

36. A method for assisting a person's gait while walking, comprising:

(a) using a sensor configured to be located at a single location on the person's torso, electronically detecting, based on time derivation of gait movements, near fall events during the gait; and (b) electronically providing periodic gait regulating cueing signals indicating a suggested gait pace while walking, responsive to said detecting near fall events, wherein said suggested gait pace includes at least one of an indication and a prompt of a regular pace for the gait;

wherein said gait movements are collected using the sensor;

wherein said electronically detecting is using a processor in communication with said sensor;

wherein said electronically providing is by a user interface.

37. A method according to claim 36, wherein the signals are at least one of audible, tactile or visual.

38. A method of gait data collection according to claim 36, wherein said cueing signals prompt the person to recover a proper gait.

39. The method according to claim 36, wherein said periodically electronically providing is based on a proper gait of a healthy person.

40. The method according to claim 36, wherein said suggested gait pace is based on intervals where the person's gait is determined to be proper.

41. An apparatus for assisting a person's gait while walking, comprising:

(a) a sensor operatively connected to the person's torso and responsive to movement of said person during the gait;

(b) a processor adapted to receive movement data from said sensor and to process said movement data to detect near fall events during the movement during the gait; and (c) at least one device operable to provide periodic cuing signals responsive to detected near fall events during the gait, wherein said cuing signals include at least one signal indicating a suggested gait pace to adjust the gait and to stabilize the gait while walking, wherein said suggested gait pace includes at least one of an indication and a prompt of a regular pace for the gait.

42. A device according to claim 41, wherein the signals are at least one of audible, tactile or visual.

43. A device according to claim 41, wherein said processor is adapted to process said movement data to detect a gait irregularity.

44. A device according to claim 41, wherein said cuing signals are selected from audible messages, audible ticks, vibrations, audible prompts, auditory stimulation, and visual stimulation.

45. The device according to claim 41, wherein said cuing signals include at least one of rhythmic tones, rhythmic alarm lights, and rhythmic indications on a display.

46. Apparatus according to claim 41, wherein said cuing signals are based on behavior detected or assessed in healthy persons.

47. Apparatus according to claim 41, wherein said suggested gate pace is based on intervals where the person's gait is determined to be proper.

* * * * *